(12) United States Patent
Mumper et al.

(10) Patent No.: US 7,803,392 B2
(45) Date of Patent: Sep. 28, 2010

(54) PH-SENSITIVE MUCOADHESIVE FILM-FORMING GELS AND WAX-FILM COMPOSITES SUITABLE FOR TOPICAL AND MUCOSAL DELIVERY OF MOLECULES

(75) Inventors: Russell Mumper, Lexington, KY (US); Michael Jay, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 496 days.

(21) Appl. No.: 09/748,133

(22) Filed: Dec. 27, 2000

(65) Prior Publication Data

US 2002/0142042 A1   Oct. 3, 2002

(51) Int. Cl.
A61F 2/02    (2006.01)
(52) U.S. Cl. ..................................... 424/423
(58) Field of Classification Search ............... 424/428, 424/484, 426, 28.04, 9.52, 430, 434, 435, 424/443
See application file for complete search history.

(56) References Cited

U.S. PATENT DOCUMENTS

| | | | |
|---|---|---|---|
| 3,922,260 A | 11/1975 | Peniston et al. | 260/211 |
| 4,517,173 A | 5/1985 | Kizawa et al. | 424/16 |
| 4,552,751 A | 11/1985 | Inaba et al. | 424/449 |
| 4,715,369 A | 12/1987 | Suzuki et al. | 128/156 |
| 4,900,554 A | 2/1990 | Yanagibashi et al. | 424/448 |
| 4,959,218 A | 9/1990 | Eckenhoff et al. | 424/473 |
| 5,081,157 A | 1/1992 | Pomerantz | 514/781 |
| 5,081,158 A | 1/1992 | Pomerantz | 514/781 |
| 5,102,666 A * | 4/1992 | Acharya | 424/487 |
| 5,192,802 A | 3/1993 | Rencher | 514/535 |

(Continued)

FOREIGN PATENT DOCUMENTS

AU    754490    10/1999

(Continued)

OTHER PUBLICATIONS

Ward, M., Direct Thrombin Inhibitors, Stanford Interventional Cardiology, Jul. 24, 2000.*

(Continued)

*Primary Examiner*—Carlos A Azpuru
(74) *Attorney, Agent, or Firm*—King & Schickli, PLLC

(57) ABSTRACT

The present invention relates to pH-sensitive mucoadhesive film-forming gels and wax-film composites suitable for topical and mucosal delivery of molecules of interest, namely active pharmaceuticals. The gels comprise a pharmaceutically acceptable pH-sensitive polymer that responds to a lowering of pH by precipitating into films when in contact with the skin or mucosal surface. The films also comprise an adhesive polymer that allows the film to remain in contact with the tissue for an extended period of time. The wax-film composites comprise a bi-layer film having both the said pH-sensitive mucoadhesive layer to promote strong adherence to the skin and mucosal surfaces as well as a specially bonded wax layer intended to extend the adherence of the film to tissues for a prolonged period of time. The invention also relates to the use of said pH-sensitive film-forming gels and wax-film composites to deliver molecules of interest, such as small molecules, peptides, proteins, and nucleic acids either locally to act at the site of administration or for the absorption of said molecules of interest across biological membranes into the systemic circulation.

15 Claims, 10 Drawing Sheets pH-Sensitive Mucoadhesive Film-Forming Gels

Composition of Gel:
- A solvent vehicle comprising at least 25% water
- Water-insoluble swellable mucoadhesive polymer(s)
- pH-sensitive film-forming polymer(s)
- Molecule of interest pH-Sensitive Mucoadhesive Wax-Film Composites Composition of Wax-Film Composite:
A*: pH-sensitive mucoadhesive layer (comprised of the components of A above less the solvent vehicle)
B: Water-insoluble wax layer with water-soluble or water-swellable polymer Note: Molecule of interest is contained in either A* or B, or both

U.S. PATENT DOCUMENTS

| | | | | |
|---|---|---|---|---|
| 5,252,318 | A | | 10/1993 | Joshi et al. ............... 424/78.04 |
| 5,298,258 | A | | 3/1994 | Akemi et al. ................ 424/484 |
| 5,314,915 | A | | 5/1994 | Rencher ..................... 514/535 |
| 5,346,701 | A | | 9/1994 | Heiber et al. ............... 424/435 |
| 5,362,737 | A | * | 11/1994 | Vora et al. .................. 514/291 |
| 5,441,732 | A | | 8/1995 | Hoeg et al. ............. 424/78.04 |
| 5,446,070 | A | * | 8/1995 | Mantelle .................. 514/772.6 |
| 5,472,704 | A | | 12/1995 | Santus et al. ............... 424/435 |
| 5,639,469 | A | * | 6/1997 | Benes et al. ............... 424/435 |
| 5,688,520 | A | | 11/1997 | Karsenty et al. ............ 424/434 |
| 5,700,478 | A | * | 12/1997 | Biegajski et al. ............ 424/434 |
| 5,780,045 | A | | 7/1998 | McQuinn et al. ............ 424/434 |
| 5,800,832 | A | | 9/1998 | Tapolsky et al. ............ 424/449 |
| 5,900,247 | A | | 5/1999 | Rault et al. ................. 424/434 |
| 5,955,097 | A | | 9/1999 | Tapolsky et al. ............ 424/434 |
| 5,989,535 | A | | 11/1999 | Nayak ..................... 424/78.02 |
| 5,993,846 | A | | 11/1999 | Friedman et al. ............ 424/434 |
| 6,004,546 | A | | 12/1999 | Sachetto .................. 424/78.01 |
| 6,086,911 | A | | 7/2000 | Godbey ....................... 424/448 |
| 6,159,498 | A | | 12/2000 | Tapolsky et al. ............ 424/434 |
| 6,210,699 | B1 | | 4/2001 | Acharya et al. ............. 424/435 |
| 6,319,510 | B1 | | 11/2001 | Yates ............................. 24/4 |
| 2002/0132008 | A1 | | 9/2002 | Mumper et al. ............ 424/78.3 |

FOREIGN PATENT DOCUMENTS

| | | |
|---|---|---|
| EP | 0 435 199 | 7/1991 |
| WO | WO98 17251 | 4/1998 |
| WO | WO 00 10536 | 3/2000 |
| WO | WO 00/54733 | 9/2000 |
| WO | WO 00 59423 | 10/2000 |

OTHER PUBLICATIONS

Aspden, T.J., Adler, J., Davis, S.S., Skaugrud, O., Illum, L. Chitosan as a nasal delivery system: evaluation of the effect of chitosan on mucociliary clearance rate in the frog palate model. *Int. J. Pharm.* 122:69-78, 1995.

Bayley, D., Temple, C., Clay, V., Steward, A., Lowther, N. The Transmucosal absorption of recombinant human interferon-alpha B/D hybrid in the rat rabbit. *J. Pharm. Pharmacol.* 47:721-724, 1995.

Berthold, A., Cremer, K., Kreuter, J. Preparation and characterization of chitosan microspheres as drug carriers for prednisolone sodium phosphate as a model for anti-inflammatory drugs. *J. Cont. Rel.* 39:17-25, 1996.

Bhatt, L.D., Johnston, T.P. In vitro release and permeation of oxytocin from a mucoadhesive buccal patch. *Pharm. Dev. Technol.* 1:357-364, 1996.

Bhatt, L.C., Johnston, T.P. Transmucosal devliery of oxytocin to rabbits using a mucoadhesive buccal patch. *Pharm. Dev. Technol.* 2:265-274, 1997.

Bodde, H.E., de Vries, M.E., Junginger, H.E. Mucoadhesive polymers for the buccal delivery of peptides, structure-adhesiveness relationships. *J. Cont. Rel.* 13:225-231, 1990.

Duchene, D., Touchard, F., Peppas, N.A. Pharmaceutical and medical aspects of bioadhesive systems for drug administration. *Drug Devol. Ind. Pharm.* 14:283-318, 1988.

Goto, S., Kawata, M., Suzuki, T., Kim, N.S., Ito, C. Preparation and evaluation of Eudragit gels. I: Eudragit organogels containing drugs as rectal sustained-release preparations. *J Pharm Sci.* 80:958-961, 1991.

Hardy, E., Jimenez, A.L., de Padue, K.S., Zaneveld, L.J. Women's preferences for vaginal antimicrobial contraceptives. III. Choice of a formulation, applicator, and packaging. Contraception. 58:245-249, 1998a.

Hardy, E., de Padu, K.S., Osis, M.J., Jimenez, A.L., Zaneveld, L.J. Women's preferences for vaginal antimicrobial contraceptives. IV. Attributes of a formulation that would protect from STD/AIDS. Contraception, 58:251-255, 1998b.

Harris, D., Robinson, J.R. Bioadhesive polymers in peptide and drug delivery. *Biomaterials*, 11:652-558, 1990.

Henriksen, I., Vagen, S.R., Sande, S.A., Smistad, G., Karlsen, J. Interactions between liposomes and chitosan II: effect of selected parameters on aggregation and leakage. *Int. J. Pharm.* 146:193-204, 1997.

Illum, L., Farraj, N.F., Davis, S.S. Chitosan as a novel nasal delivery system for peptide drugs. *Pharm. Res.* 11:1186-1189, 1994.

Imai, T., Shiraishi, S., Saito, H., Otagiri, M. Interaction of indomethacin with low molecular weight chitosan, and improvements of some pharmaceutical properties of indomethacin by low molecular weight chitosans. *Int. J. Pharm.* 67:11-20, 1991.

Kawata, M., Suzuki, T., Kim, N.S., Ito, T., Kurita, A., Miyagoe, Y., Goto, S. Preparation and evaluation of Eudragit gels. II: In vitro release of salicylic acid, sodium salicylate, and ketoprofen from Eudragit L and S organogels. *J Pharm Sci.* 80:1072-1074, 1991.

Khan, M.Z., Prebeg, Z., Kurjakovic, N. A pH-dependent colon targeted oral drug delivery system using methacrylic acid copolymers. I. Manipulation of drug release using Eudragit L100-55 and Eudragit S100 combinations. *J Controlled Release.* 58:215-22, 1999.

Kim, N.S., Umejima, H., Ito, T., Uchida, T., Goto, S. Preparation and evaluation of Eudragit gels. V. Rectal gel preparations for sustained release and avoidance of first-pass metabolism of lidocaine. *Chem Pharm Bull.* 40:2800-2804, 1992a.

Kim, N.S., Ito, T., Kawata, M., Uchida, T., Goto, S. Preparation and evaluation of Eudragit gels. IV: Rectal gel preparations for sustained release and avoidance of first-pass metabolism of propentofylline. *J Pharm Sci.* 81:904-907, 1992b.

Kim, N.S., Kawata, M., Uchida, T., Goto, S. Preparation and evaluation of Eudragit gels. III: Rectal gel preparations for sustained release of pentoxifylline. *J Pharm Sci.* 81:537-40, 1992.

Lehr, C.M., Bouwstra, J.A., Schacht, E., Junginger, H.E. In vitro evaluation of mucoadhesive properties of chitosan and some other natural polymers. *Int. J. Pharm.* 78:43-48, 1992.

MacLaughlin, F.C, Mumper, R.J., Wang, J., Tagliaferri, J.M., and Rolland, A.P. Chitosan and depolymerized chitosan oligomers as condensing carriers for in-vivo plasmid delivery. *J. Controlled Rel.* 56:259-272, 1998.

Meshali, M.M., Gabr, K.E. Effect of interpolymer complex formation of chitosan with pectin or acacia on the release behavior of chlorpromazine HCl. *Int. J. Pharm.* 89:177-181, 1993.

Sayani, A.P., Chun, I.K., Chien, Y.W. Transmucosal delivery of leucine enkephalin: stabilization in rabbit enzyme extracts and enhancement of permeation through mucosae. *J. Pharm. Sci.* 82:1179-1185, 1993.

Schipper, N.G.M., Varum, K.M., Artursson, P. Chitosans as absorption enhancers for poorly absorbable drugs. I: influence of molecular weight and degree of acetylation on drug transport across human intestinal epithelial (Caco-2) cells. *Pharm. Res.* 13:1686-1692, 1996.

Scott, R.C., Besag, F.M.C., Neville, B.G.R. Buccal midazolam and rectal diazepam for treatment of prolonged seizures in childhood and adolescence: a randomized trial. *The Lancet.* 353:623-626, 1999.

Shiraishi, S., Imai, T., Otagiri, M. Controlled release of indomethacin by chitosan-polyelectrolyte complex: optimization and in vivo/in vitro evaluation. *J. Cont. Rel.* 25:217-225, 1993.

Takayama, K., Hirata, M., Machida, Y., Masada, T., Sannan, T., Nagai, T. Effect of interpolymer complex formation on bioadhesive property and drug release phenomenon of compressed tablet consisting of chitosan and sodium hyaluronate. *Chem. Pharm. Bull.*, 38:1993-1997, 1990.x.

Takeuchi, H., Yamamoto, H., Niwa, T., Hino, T., Kawashima, Y. Enteral absorption of insulin in rats from mucoadhesive chitosan-coated liposomes. *Pharm. Res.* 13:896-901, 1996.

Umejima, H., Kim, N.S., Ito, T., Uchida, T., Goto, S. Preparation and evaluation of Eudragit gels. VI: In vivo evaluation of Eudragit rectal hydrogel and xerogel containing salicylamide. *J Pharm Sci.* 82:195-9, 1993.

Wong, C.F., Yuen, K.H., Peh, K.K. Formulation and evaluation of controlled release Eudragit buccal patches. *Int. J. Pharmaceutics.* 178:11-22, 1999.

Bechgaard et al., "Solubilization of various benzodiazepines for intranasal administration, a pilot study," *Pharm Dev Tech*, 2:293-296, 1997.

Binnie et al., "Amlexanox oral paste: a novel treatment that accelerates the healing of aphthous ulcers," *Compend Contin Educ Dent*, 18:1116-1118, 1997.

Casetta and Negretti, "Salivary immune responses after gingival immunization with tetravaccinal and bivaccinal formulations of inactivated micro-organisms," *Dev Biol Stand*, 92:317-321, 1998.

Chang, "Stability of hirudin, a thrombin-specific inhibitor," *J Biol Chem*, 266:10839-10843, 1991.

Eric and Caroline, "Influence of storage conditions on the activity of recombinant hirudin," *Thromb Res*, 61:87-89, 19991.

Eriksson et al., "Prevention of thromboembolism with use of recombinant hirudin. Results of a double-blind, multicenter trial comparing the efficacy of desirudin (Revasc) with that of unfractionated heparin in patients having total hip replacement," *J Bone Joint Surg Am*, 79:326-333, 1997.

Esslinger et al., "Pharmacodynamic and safety results of PEG-hirudin in healthy volunteers," *Throm Haemost*, 77:911-919, 1997.

Etchart et al., "Class I-restricted CTL induction by mucosal immunization with naked DNA encoding measles virus hemagglutinin," *J Gen Virol*, 78:1577-1580, 1997.

Fenton et al., "Thrombin inhibition by hirudin: how hirudin inhibits thrombin," *Haemostasis*, 21:27-31, 1991.

Fenton, "Thrombin interactions with hirudin," *Sem Thromb Hemost*, 15:265-268, 1989.

Garcia-Closas et al., "Epidemiologic determinants of vaginal pH," *Am J Obstet Gynecol*, 180:1060-1066, 1999.

Heath et al., "Mechanism of triclosan inhibition of bacterial fatty acid synthesis," *J Biol Chem*, 274:11110-11114, 1999.

Hjortkjaer et al., "Single- and repeated-dose local toxicity in the nasal cavity of rabbits after intransal administration of different glycols for formulations containing benzodiazepines," *J Pharm Pharmacol*, 51:377-383, 1999.

Jones et al., "Targeting and delivery of batericide to adsorbed oral bacteria by use of proteoliposomes," *Biochim Biophys Acta*, 1147:251-261, 1993.

Khandwala et al., "5% amlexanox oral paste, a new treatment for recurrent minor aphthous ulcers: I. clinical demonstration of acceleration of healing and resolution of pain," *Oral Surg Oral Med Oral Pathol Oral Radiol Endod*, 83:222-230, 1997a.

Khandwala et al., "5% amlexanox oral paste, a new treatment for recurrent minor aphthous ulcers: II. Pharmacokinetics and demonstration of clinical safety," *Oral Surg Oral Med Oral Pathol Oral Radiol Endod*, 83:231-238, 1997b.

Leopold and Eikeler, "Eudragit E as a coating material for the pH-controlled drug release in the topical treatment of inflammatory bowel disease (IBD)," *J Drug Targeting*, 6:85-94, 1998.

Leung et al., "Mucoadhesive dosage froms for peptide and protein drug delivery," In: *Peptide and Protein Drug Delivery*, V.H.L. Lee ed. Marcel Dekker, Inc. New York, pp. 741-767, 1991.

Liu et al., "DNA vaccines: A new era in vaccinology," *Ann NY Acad Sci, New York, NY*, 772. 1995.

Loftsson et al., "Effect of cyclodextrins and polymers on triclosan availability and substantivity in toothpastes in vivo," *J Pharm Sci*, 88:1254-1258, 1999.

Mandel, "Antimicrobial mouthrinses: overview and update," *J Am Dent Assoc*, 125:2S-10S, 1994.

March and Nakamura, "Evaluation of the duration of effect of a bioadhesive vaginal moisturizing get on vaginal pH," *7th International Congress on the Menopause, Replens Symposium, Stockholm, Sweden*, Jun. 20-22, 1993.

Markwardt, "Development of hirudin as an antithrombotic agent," *Sem THromb Hemost*, 15:269-282, 1989.

Markwardt, "Past, present and future of hirudin," *Haemostatis*, 21:11-26, 1991b.

Markwart, "Hirudin and derivatives as anticoagulant agents," *Thromb Haemost*, 66:141-152, 1991a.

Martin et al., *Martin's Physical Pharmacy: Physical chemical principles in the pharmaceutical sciences*, Lea & Febiger, Third Ed., Philidelphia, 1983.

McGhee and Kiyono, "Mucosal immunity to vaccines: Current concepts for vaccine development and immune reponse analysis," In: J.E. Ciardi (ed.) *Genetically engineered vaccines*, Plenum Press, New York, NY, pp. 3-12, 1992a.

Park and Robinson, "Physico-chemical properties of water insoluble polymers important to mucin/epithelial adhesion," *J Cont Rel*, 2:47-57, 1985.

Rathbone et al., In: *Oral J Mucosal Drug Delivery*, M.J. Rathbone Ed., Marcel Dekker Inc., New York, 1996.

*Remington's Pharmaceutical Sciences*, 18th Ed., A.R. Gennard, ed. Mack Publishing Company, Easton, PA, 1990.

Riehl-Bellon et al., "Purification and biochemical characterization of recombinant hirudin produced by Saccharomyces cerevisiae," *Biochemistry*, 28:2941-2949, 1989.

Robinson and Torres, "C.A.T. DNA Vaccines," *Sem Immun*, 9:271-283, 1997.

Saijo et al., "Inhibition by amoxanox (AA-673) of the immunologically, leukotriene D4- or platelet-activating factor-stimulated bronchoconstriction in guinea pigs and rats," *Int Arch Allergy Appl Immunol*, 77:315-321, 1985.

Saijo et al., "The antiallergic agent amoxanox suppresses SRS-A generation by inhibiting lipoxygenase," *Int Arch Allergy Appl Immunol*, 79:231-237, 1986.

Schwagmeier et al., "Midazolam pharmaockinetics following intravenous and buccal administration," *Br J Clin Pharmaocl*, 46:203-206, 1998.

Spannagl et al., "A fast photometric assay for the determination of hirudin," *Haemostasis*, 21:36-40, 1991.

Stevens-Simon et al., "Racial vatiation oin vaginal pH among healthy sexually active adolescents," *Sex Trasm Dis*, 21:168-172, 1994.

Tang et al., "Genetic immunization is a simple method of eliciting an immune response," *Nature*, 356:152-154, 1992.

Taubes, "Salvation in a snippet of DNA," *Science*, 278:1711-1714, 1997.

Ulmer et al., "Toward the development of DNA vaccines," *Curr Opin Immun*, 8:531-536, 1996a.

Urisu et al., "Inhibitory action amlexanox on interleukin-3-induced enhancement of histamine releasability of human leukocytes," *Arerugi*, 39(10):1448-1454, 1990. (ABSTRACT).

Yankauckas et al., "Long-term anti-nucleoprotein cellular and humoral immunity is induced by intramuscular injection of plasmid DNA containing NP gene," *DNA Cell Biol*, 12:771-776, 1993.

Zuckerbraun et al., "Triclosan: cytotoxicity, mode of action, and induction of apoptosis in human gingival cells in vitro," *Eur J Oral Sci*, 106:628-636, 1998.

Co-Pending U.S. Appl. No. 10/072,320, filed Feb. 7, 2002, (NANO:002USD1).

Nakumura et al., "Uptake and release of budesonide from nucoadhesive, pH-sensitive copolymers and their application to nasal delivery", *J Controlled Release*, 61(3):329-35, 1999.

Park and Robinson., "Mechanisms of mucoadhesion of poly(acrylic acid) hydrogels", *Pharm Res*, 4:457-64, 1987.

Ramkissoon-Ganorkar et al., "Effect of molecular weight and polydispersity on kinetics of dissolution and release from ph/temperature-sensitive polymers", *J Biomater Sci Polym Ed*, 10(10):1149-61, 1999.

Ryu JM et al., "Increased bioavailability of propranolol in rats by retaining thermally gelling liquid Oersuppositories in the rectum", *J Controlled Release*, 59(2):163-72, 1999.

International Preliminary Examination Report issued in International Application No. PCT/US01/49524, completed Feb. 24, 2004.

International Search Report issued in International Application No. PCT/US01/49524, mailed Jan. 24, 2003.

Office Action issued in Canadian Application No. 2,437,150, mailed Aug. 15, 2008.

Office Action issued in European Application No. 01 991 430.8, mailed Oct. 2, 2008.

Office Action issued in European Application No. 01 991 430.8, mailed Dec. 4, 2006.

Office Action issued in U.S. Appl. No. 10/072,320, mailed Nov. 17, 2004.

Office Action issued in U.S. Appl. No. 10/072,320, mailed Feb. 2, 2004.

\* cited by examiner pH-Sensitive Mucoadhesive Film-Forming Gels

Composition of Gel:

- A solvent vehicle comprising at least 25% water
- Water-insoluble swellable mucoadhesive polymer(s)
- pH-sensitive film-forming polymer(s)
- Molecule of interest

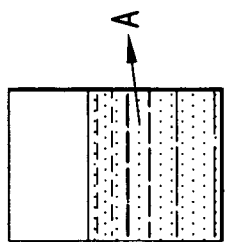

pH-Sensitive Mucoadhesive Wax-Film Composites

Composition of Wax-Film Composite:

A*: pH-sensitive mucoadhesive layer (comprised of the components of A above less the solvent vehicle)

B: Water-insoluble wax layer with water-soluble or water-swellable polymer

Note: Molecule of interest is contained in either A* or B, or both

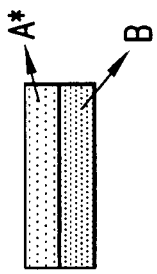

FIG.1

PH-SENSITIVE MUCOADHESIVE FILM-FORMING GELS AND WAX-FILM COMPOSITES SUITABLE FOR TOPICAL AND MUCOSAL DELIVERY OF MOLECULES

FIELD OF THE INVENTION

The present invention relates to compositions and methods to treat the skin and mucosal surfaces with mucoadhesive film-forming gels and wax-film composites that are pH-sensitive. The invention also relates to using such pH-sensitive film-forming gels and wax-film composites to deliver molecules of interest, namely active pharmaceuticals. The invention also relates to the use of said pH-sensitive film-forming gels and wax-film composites to deliver molecules of interest, such as small molecules, peptides, proteins, and nucleic acids either locally to act at the site of administration or for the absorption of said molecules of interest across biological membranes into the systemic circulation.

BACKGROUND OF THE INVENTION

Pharmaceutical formulations intended to deliver drugs topically, either for local action at the site of administration or for absorption into the systemic circulation, have been described in the literature. These formulations are designed either for adherence of the dosage form to the skin (for dermal or transdermal delivery of drugs) or mucosal surface (for mucosal or transmucosal delivery of drugs). For skin delivery, formulations generally consist of dermal patches, pastes, band-aids, gels, lotions, sprays, or creams. For mucosal delivery, formulations generally consist of gels, creams, tablets, sprays, or films. In either case, one specific requirement is that the dosage form remains at the administration site for a sufficient amount of time so that the drug may function as needed. A second specific requirement is that the dosage form must consist of pharmaceutically acceptable materials. Many of the reported and commercially available delivery systems intended for topical and mucosal delivery are aqueous-based formulations comprising water-soluble excipients. However, these systems tend to be easily and quickly washed away from the application site within minutes after application. This is very undesirable if the drug must remain at the application site for a prolonged period in order to be efficacious. In an attempt to prolong the residence time at the application site, researchers have described the use of water-insoluble excipients in the formulations. However, most often the use of water-insoluble excipients necessitates the use of non-aqueous solvents to dissolve the excipients. Excessive and repeated administration of non-aqueous solvents is not desirable.

Different types of formulations to deliver drugs topically are known in the art. Specific examples are illustrated below.

U.S. Pat. No. 4,715,369 by Suzuki et al. relates to methods to treat the injured oral mucosa with a thin two-layer tablet comprised of both an adhesive layer and a nonadhesive layer. The adhesive layer is comprised of water-soluble cellulose-based polymers and polyacrylic acid while the nonadhesive layer is comprised mostly of materials with no adhesive properties. The Suzuki patent does not teach the use of film-forming gels comprised of pH-sensitive polymers and water-insoluble mucoadhesive polymers that form films due to changes in pH and/or desolvation of the polymers. Further, the Suzuki patent does not teach the use of pH-sensitive wax-film composites intended to remain adhered to the skin or mucosal surface for a prolonged period of time.

U.S. Pat. No. 5,800,832 by Tapolsky et al. relates to a water-soluble, bioerodable device for the delivery of drugs, and specifically dyclonine, to mucosal surfaces. The device comprises an adhesive layer as well as a non-adhesive layer. Both the adhesive layer and the nonadhesive layer consist of water-soluble polymers such as cellulose-based polymers. The Tapolsky patent does not teach the use of film-forming gels comprised of pH-sensitive polymers and water-insoluble mucoadhesive polymers that form films due to changes in pH and/or desolvation of the polymers. Further, the Tapolsky patent does not teach the use of pH-sensitive wax-film composites intended to remain adhered to the skin or mucosal surface for a prolonged period of time.

U.S. Pat. No. 5,955,097 by Tapolsky et al. relates to a non water-soluble gel, which adheres to mucosal surfaces and body tissues upon application and forms a film. The gel comprises at least one water-insoluble cellulose-based polymer, a non-aqueous solvent, and at least one active pharmaceutical. The patent teaches that upon application to the mucosal surface or skin, the non-aqueous solvent, primarily ethanol, evaporates, diffuses, or penetrates the surrounding tissue, resulting in precipitation of the non water-soluble polymers into films. The Tapolsky patent further teaches the use of 50 to 80% ethanol by weight in the pharmaceutical gel. The Tapolsky patent does not teach the use of film-forming gels containing at least 25% water by weight and comprised of pH-sensitive polymers and water-insoluble mucoadhesive polymers that form films due to changes in pH and/or desolvation of the polymers. Further, the Tapolsky patent does not teach the use of pH-sensitive wax-film composites intended to remain adhered to the skin or mucosal surface for a prolonged period of time.

U.S. Pat. No. 5,780,045 by McQuinn et al. relates to a transmucosal drug delivery device in the form of a sheet comprising an acid-containing particulate polymer dispersed in a polytetrafluoroethylene support matrix. The McQuinn patent does not teach the use of film-forming gels comprised of pH-sensitive polymers and water-insoluble mucoadhesive polymers that form films due to changes in pH and/or desolvation of the polymers. Further, the McQuinn patent does not teach the use of pH-sensitive wax-film composites intended to remain adhered to the skin or mucosal surface for a prolonged period of time.

U.S. Pat. No. 4,552,751 by Inaba et al. relates to the preparation of multi-layered films of three, five, or seven layers for the administration of specific prostaglandins to mucosal sites. The Inaba patent does not teach the use of film-forming gels comprised of pH-sensitive polymers and water-insoluble mucoadhesive polymers that form films due to changes in pH and/or desolvation of the polymers. Further, the Inaba patent does not teach the use of pH-sensitive wax-film composites intended to remain adhered to the skin or mucosal surface for a prolonged period of time.

U.S. Pat. No. 4,517,173 by Kizawa et al. relates to a film preparation consisting of at least three layers, including a pharmaceutical layer, a poorly water-soluble layer, and an intermediate layer. The pharmaceutical layer consists of predonisolone and allantoin together with a water-soluble cellulose-based polymer. The poorly water-soluble layer consists of shellack or fatty acids. The Kizawa patent does not teach the use of film-forming gels comprised of pH-sensitive polymers and water-insoluble mucoadhesive polymers that form films due to changes in pH and/or desolvation of the polymers. Further, the Kizawa patent does not teach the use of pH-sensitive wax-film composites intended to remain adhered to the skin or mucosal surface for a prolonged period of time.

U.S. Pat. No. 5,192,802 by Rencher describes the use of a bioadhesive teething gel comprising benzocaine, sodium carboxy methyl cellulose; an agent selected from the group consisting of xanthan gum and sodium alginate and a diluent selected from the group consisting of polyethylene glycol and polyethylene glycol with glycerine. U.S. Pat. No. 5,314,915 by Rencher and U.S. Pat. No. 5,298,258 by Akemi et al. also describe the use of aqueous or oil-based bioadhesive gelling agents. These patents do not teach the use of film-forming gels comprised of pH-sensitive polymers and water-insoluble mucoadhesive polymers that form films due to changes in pH and/or desolvation of the polymers. Further, these patents do not teach the use of pH-sensitive wax-film composites intended to remain adhered to the skin or mucosal surface for a prolonged period of time.

U.S. Pat. Nos. 5,081,157 and 5,081,158 by Pomerantz relate to a film-forming composition for topical application of medicaments to body tissues. The film-forming composition includes hydroxypropyl cellulose, a volatile solvent, and an esterification agent which reacts with the hydroxypropyl cellulose to form a reaction product which is soluble in the solvent. These patents do not teach the use of film-forming gels comprised of pH-sensitive polymers and water-insoluble mucoadhesive polymers that form films due to changes in pH and/or desolvation of the polymers. Further, these patents do not teach the use of pH-sensitive wax-film composites intended to remain adhered to the skin or mucosal surface for a prolonged period of time.

U.S. Pat. No. 4,900,554 by Yanagibashi et al. relate to the use of a device for the delivery of drugs in the oral cavity. The device comprises an adhesive layer consisting of at least one acrylic acid polymer, a water-insoluble cellulose derivative, and a pharmaceutical preparation, and a water-insoluble or sparingly soluble backing layer. Yanagibashi et al. state that "it is impossible to achieve an adhesive device for application to body tissue without all three components, that is, acrylic acid polymer, water insoluble cellulose derivative and water insoluble or sparingly soluble backing layer". The Yanagibashi patent does not teach the use of film-forming gels comprised of pH-sensitive polymers and water-insoluble mucoadhesive polymers that form films due to changes in pH and/or desolvation of the polymers. Further, the Yanagibashi patent does not teach the use of pH-sensitive wax-film composites intended to remain adhered to the skin or mucosal surface for a prolonged period of time.

As illustrated, the references described above appear to lack preferred compositions and properties for an efficacious and pharmaceutically acceptable bioadhesive delivery system. Namely, the references do not describe primarily aqueous-based film-forming gels comprised of pH-sensitive polymers and water-insoluble mucoadhesive polymers that form films due to changes in pH and/or desolvation of the polymers. Further, the references do not describe pH-sensitive mucoadhesive wax-film composites intended to remain adhered to the skin or mucosal surface for a prolonged period of time.

SUMMARY OF THE INVENTION

The invention is directed to a pharmaceutical gel composition comprising:
  a solvent vehicle,
  at least one water-insoluble swellable mucoadhesive polymer,
  at least one pH-sensitive film-forming polymer, and
  at least one molecule of interest.

The solvent vehicle may be comprised of at least 25 to 100 parts water or buffered water with 0 to 75 parts of ethanol, propylene glycol, glycerin, polyethylene glycol, or combinations thereof. The water-insoluble swellable mucoadhesive polymer may be polyacrylic acid cross-linked with polyalkenyl ether or divinyl glycol, wherein the water-insoluble swellable mucoadhesive polymer is preferably, NOVEON or CARBOMER. The water-insoluble swellable mucoadhesive polymer may be present at a concentration of from 0.1% to 20% by weight.

The pH-sensitive polymer is a copolymer of methacrylic acid and acrylic or methacrylic ester. Preferably, it is present at a concentration of from 0.05% to 10% by weight. More preferably, the polymer is a Eudragit polymer, or a chemical derivative thereof.

The molecule of interest may comprise an active pharmaceutical such as an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or combination thereof. Preferably, the molecule of interest is amlexanox, triclosan, peptide, protein, hirudin, plasmid DNA, lidocaine, benzocaine, dyclonine, or benzodiazepine drug or a derivative thereof.

The invention is also directed to a pharmaceutical gel which when applied to the skin or mucosal surface forms a film, said gel comprising a solvent vehicle, at least one water-insoluble swellable mucoadhesive polymer, at least one pH-sensitive film-forming polymer, and at least one molecule of interest, wherein said film is formed due to changes in pH and desolvation of the polymer, and wherein said film provides for the delivery of the molecule of interest to or through the application site. The solvent vehicle may be comprised of at least 25 to 100 parts water with 0 to 75 parts of ethanol, propylene glycol, glycerin, polyethylene glycol, or combinations thereof. The water-insoluble swellable mucoadhesive polymer may be polyacrylic acid cross-linked with polyalkenyl ether or divinyl glycol. Preferably, the water-insoluble swellable mucoadhesive polymer is NOVEON or CARBOMER. The water-insoluble swellable mucoadhesive polymer may be present at a concentration of from 0.1% to 20% by weight.

The pH-sensitive polymer may be a copolymer of methacrylic acid and acrylic or methacrylic ester. Preferably, it is present at a concentration of from 0.05% to 10% by weight. More preferably, the polymer is a Eudragit polymer, or a chemical derivative thereof.

The molecule of interest may comprise an active pharmaceutical such as an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or combination thereof. Preferably, the molecule of interest is amlexanox, triclosan, peptide, protein, hirudin, plasmid DNA, lidocaine, benzocaine, dyclonine, or benzodiazepine drug or a derivative thereof. The application site may be the skin, mouth, vagina, nose, nasal cavity, or other accessible mucosal site.

The invention is also directed to a wax-film composite comprised of a pH-sensitive mucoadhesive layer and a water-insoluble wax layer. The pH-sensitive mucoadhesive layer may be present at a concentration of 20% to 90% by weight, and the water-insoluble wax layer may be present at a concentration of 10% to 80% by weight. The pH-sensitive mucoadhesive water-insoluble layer may be comprised of:
  at least one water-insoluble swellable mucoadhesive polymer, at least one pH-sensitive film-forming polymer, and at least one molecule of interest.

The water-insoluble swellable mucoadhesive polymer may be polyacrylic acid cross-linked with polyalkenyl ether or divinyl glycol. Preferably, the water-insoluble swellable mucoadhesive polymer is NOVEON or CARBOMER. The water-insoluble swellable mucoadhesive polymer may be present at a concentration of from 0.1% to 20% by weight.

The pH-sensitive polymer may be a copolymer of methacrylic acid and acrylic or methacrylic ester. Preferably, it is present at a concentration of from 0.05% to 10% by weight. More preferably, the polymer is a Eudragit polymer, or a chemical derivative thereof.

The molecule of interest may comprise an active pharmaceutical such as an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or combination thereof. Preferably, the molecule of interest is amlexanox, triclosan, hirudin, plasmid DNA, lidocaine, benzocaine, dyclonine, or benzodiazepine drug or a derivative thereof. The wax-film composite may comprise at least one water-insoluble pharmaceutical wax having a melting point between 40° C. and 100° C. and at least one water-soluble or water-swellable polymer.

The wax may be DENTSPLY® Utility Wax (Dentsply Prosthetics, York, Pa.), beeswax, emulsifying wax, microcrystalline wax, carnauba wax, paraffin wax, white wax, yellow wax, or other suitable pharmaceutical wax. The water-soluble or swellable polymer may be present in the insoluble wax layer at a concentration of 0.05 to 10% by weight. The water-soluble or swellable polymer may be tragacanth, polyvinyl pyrrolidone, polyvinyl alcohol, cross-linked polyacrylic acid, polyethylene glycol, a cellulose polymer derivative, or other suitable pharmaceutical polymer that is water-soluble or water-swellable. In the wax-film composite, the molecule of interest may be contained in and released from either the pH-sensitive mucoadhesive layer or the water-insoluble wax layer.

The molecule of interest comprises an active pharmaceutical compound such as an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or a combination thereof. The molecule of interest may comprise an active pharmaceutical such as an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or combination thereof. Preferably, the molecule of interest is amlexanox, triclosan, protein, peptide, hirudin, plasmid DNA, lidocaine, benzocaine, dyclonine, or benzodiazepine drug or a derivative thereof. Preferably, the hirudin may be complexed with a substance of opposite charge. More preferably, the substance of opposite charge may be chitosan or protamine. Alternatively, the molecule of interest may be a plasmid DNA or plasmid DNA complexed with a substance of opposite charge such as chitosan, protamine, or a cationic lipid.

The application site for the wax-film composite may be the skin, mouth, vagina, nasal cavity, or other accessible mucosal site. Preferably, the wax-film composite adheres to the application site for at least 1 hour. Preferably, the wax-film composite has a total thickness of less than 5 mm.

The invention is also directed to a method of making the above pharmaceutical gel composition, comprising:
  (i) adding a mucoadhesive polymer to a stirring water to form a solution that is clear and viscous,
  (ii) adding the pH-sensitive film-forming polymer to the solution formed in step (i) and measuring the pH of the solution,
  (iii) adding the molecule of interest to the solution of step (ii), and
  (iv) forming the final gel composition.

The invention is also directed to a method of making the above wax-film composite, comprising:
  (i) forming a homogeneous mucoadhesive film by fusing a mucoadhesive polymer and a pH-sensitive film-forming polymer,
  (ii) homogeneously coating one side of the mucoadhesive film of step (i) with a melted wax composition, and
  (iii) drying the wax composition to form the wax-film composite, wherein the molecule of interest is added in either step (i) or (ii), or the molecule of interest is added to the mucoadhesive side after the wax-film composite is formed.

Furthermore, the invention is also directed to a method of treating a disease or an illness by administering to a person in need thereof, the gel or the wax-film composite as described above comprising a molecule of interest.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein;

FIG. 1 shows a summary of the compositions of the invention

DETAILED DESCRIPTION OF THE INVENTION

Figure 2:
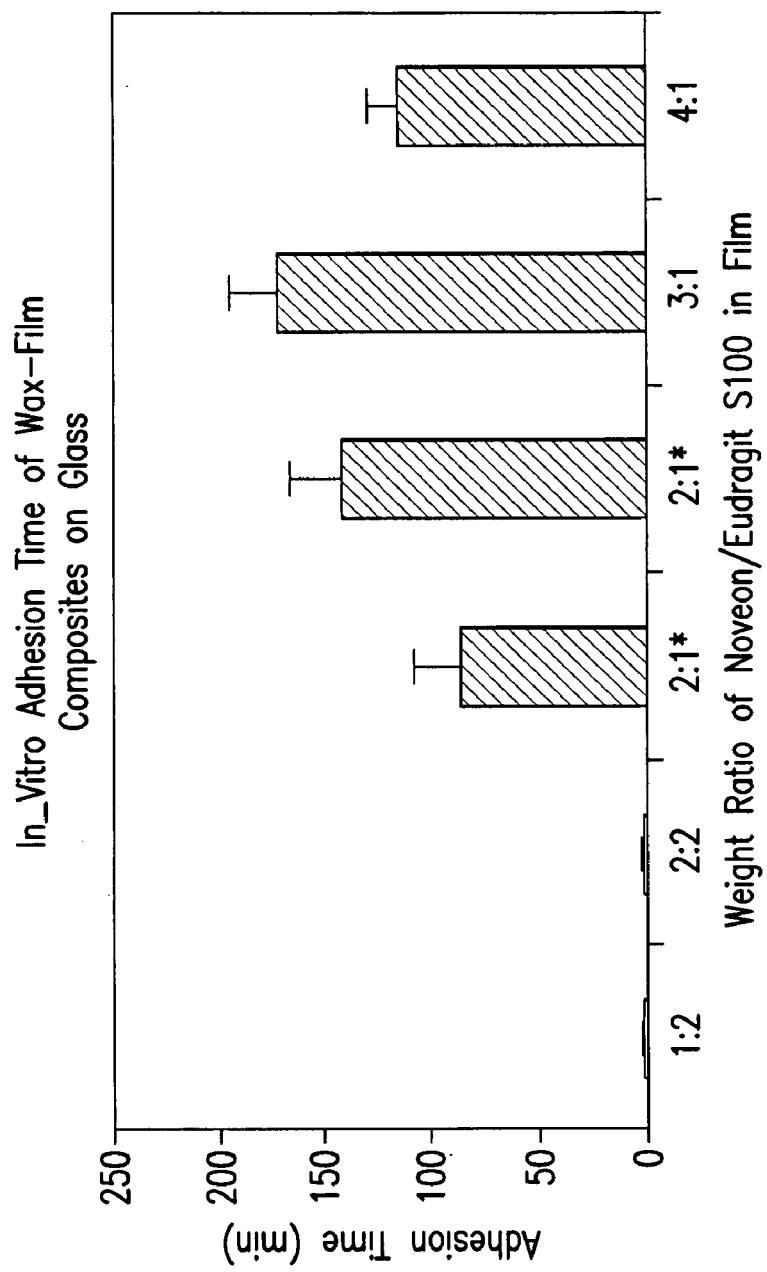
FIG. 2 shows an in vitro adhesion time of ¼ inch wax-film composites (n=3 each) on glass submerged in 40 mM $KH_2PO_4$/NaOH buffer, pH 6 at 37° C. (unstirred). Each mucoadhesive layer contains 5.0–5.3 mg of total polymer comprised of NOVEON and EUDRAGIT S100 in the ratios indicated. The wax layer consists of DENTSPLY® Utility Wax containing 1% w/w tragacanth polymer. *Indicates that different volumes of mucoadhesive gels were cast as described in Example 8. See Table 1 and Example 8 for additional details.

The invention relates to delivery systems suitable for the topical and mucosal delivery of molecules of interest. Specifically, the invention relates to; 1) compositions of pH-sensitive mucoadhesive film-forming gels, 2) uses of pH-sensitive mucoadhesive film-forming gels, 3) compositions of pH-sensitive mucoadhesive wax-film composites, and 4) uses of pH-sensitive mucoadhesive wax-film composites. A summary of the compositions of the invention is shown in FIG. 1.

The pH-sensitive mucoadhesive film-forming gel is a pharmaceutical gel which when applied to the skin or mucosal surface forms a film, said gel comprising a solvent vehicle, at least one water-insoluble swellable mucoadhesive polymer, at least one pH-sensitive film-forming polymer, and at least one molecule of interest, said film forming due to changes in pH and desolvation of the polymer, said film providing for the delivery of the molecule of interest to or through the application site.

The pH-sensitive mucoadhesive wax-film composite is a bi-layer pharmaceutical film less than 5 mm in diameter that when applied to the skin or mucosal surface adheres to the application for at least 1 hour. The wax-film composite is comprised of a pH-sensitive mucoadhesive layer and a water-insoluble wax layer.

Definitions and Preferred Embodiments

As used herein, certain terms may have the following defined meanings.

As used in the specifications and claims, the singular form a, an and the include plural references unless the context clearly dictates otherwise. For example, the term a pharmaceutical may refer to one or more pharmaceuticals for use in the presently disclosed formulations and methods.

The term molecule of interest is defined as any synthetic or naturally occurring substance including elements, radioactive elements, synthetic or natural small molecules, peptides, proteins, nucleic acids, or any combinations thereof.

The term active pharmaceutical means any synthetic or naturally occurring substance including elements, radioactive elements, synthetic or natural small molecules, peptides, proteins, nucleic acids, or any combinations thereof intended to be administered to a warm-blooded mammal to elicit a pharmacological response. The terms pharmaceutical, active pharmaceutical, and drug as used herein are identical in meaning and thus are used interchangeably. It is preferred that the active pharmaceutical be an anti-microbial, antiviral, anti-inflammatory, antiseptic, antihistamine, tranquilizer, sedative, anti-nausea, local anesthetic, disinfectant, keratolytic, analgesics including anti-migraine, anti-fungal, sweetener, flavoring agent, diagnostic agent, peptide, protein, antigen, monoclonal antibody, polyclonal antibody, nucleic acid, or combinations thereof. More preferably, the active pharmaceutical is amlexanox, triclosan, lidocaine, dyclonine, benzocaine, a benzodiazepine, hirudin, antisense oligonucleotide, or plasmid DNA, or any derivative or combinations thereof.

Amlexanox: The chemical name of Amlexanox is 2-amino-7-(1-methylethyl)-5-oxo-5H-[1]benzopyrano-[2,3-b]-pyridine-3-carboxylic acid. Amlexanox is the active ingredient in the commercial product, Aphthasol, which accelerates the healing of aphthous ulcers in the mouth by an unknown mechanism (Binnie et al. 1997; Khandwala et al. 1997a; Khandwala et al. 1997b). The Aphthasol product is a 5% paste. In cell culture experiments, Amlexanox has been shown to inhibit the formation or release of inflammatory mediators such as histamine and leukotrienes from mast cells, neutrophils, and mononuclear cells (Urisu et al. 1990). Further, in animals, Amlexanox has anti-allergic and anti-inflammatory properties and has been shown to inhibit both immediate and delayed hypersensitivity reactions (Saijo et al. 1985; Saijo et al. 1986). Amlexanox has very poor solubility in ethanol (0.58 mg/mL) and water (0.005 mg/mL). However, the solubility of Amlexanox increases with pH.

Triclosan: The chemical name of Triclosan is 2,4,4'-Trichloro 2'-hydroxy-diphenyl-ether 5-chloro 2-(2,4-dichlorophenoxy)-phenol. Triclosan is a broad-spectrum antibacterial that has activity against a wide range of gram-positive and gram-negative bacteria (Zuckerbraun et al. 1998). Triclosan has been shown to inhibit bacterial fatty acid synthesis at the enoyl-acyl carrier protein reductase (FabI) step (Heath et al. 1999). It has gained wide-spread use as antibacterial agent that is used in toothpastes, kitchen utensils and toys. Triclosan has also been formulated in mouthwashes (Mandel 1994) and liposomes (Jones et al. 1993). Triclosan has a pKa of 7.9 and is insoluble in water, except in alkaline solutions where it is readily soluble (Loftsson et al. 1999). However, triclosan is soluble in ethanol and polyethylene glycol 400 and many other organic solvents.

Hirudin: Hirudin is the most potent and specific known inhibitor of thrombin ($K_i$=0.2 pM) (Markwardt 1989; Markwardt 1991a; Markwardt 1991b; Fenton et al. 1991). Hirudin was originally isolated from medicinal leeches (Hirudo medicinalis), but is now available in large quantities due to recombinant techniques (Riehl-Bellon et al. 1989). Unlike heparin, hirudin does not require endogenous cofactors to function and does not have associated bleeding complications. Hirudin is a relatively small 65 amino acid peptide (Mw 7000) with remarkable stability over a broad range of pH (pH 3–10), temperature (i.e., up to 60° C.), and solvent conditions (Chang 1991; Eric and Caroline 1991). The main structure of hirudin is characterized by an apolar disulfide knot with a very anionic (negatively-charged) tail. The apolar knot of hirudin masks the catalytic site of thrombin by interacting with its apolar site (i.e., via hydrophobic interaction). The anionic tail of hirudin (18 amino acids) interacts with the anion-binding exosite of thrombin. It is the combination of the apolar binding and the anion-binding that accounts for the very high affinity of hirudin and thrombin. The presence of the apolar knot and anionic tail on hirudin results in both hydrophobic and hydrophilic surface interactions. For example, in solution, hirudin forms micellar complexes (e.g., tetramers) with itself. Further, the apolar region of hirudin is known to interact with cell membranes while the anionic tail remains extracellular (Fenton 1989). It is likely that the anionic portion of hirudin is electrostatically repelled from the surface of cell membranes. Novartis Pharma obtained marketing approval in the European Union in 1998 for REVASC (desirudin; recombinant hirudin) for the prevention of deep-vein thrombosis following knee and hip replacement surgery. In clinical trials, patients receiving hirudin by subcutaneous injection twice a day for 8 days had a nearly 30% lower overall rate of deep-vein thrombosis than those who received low molecular weight heparin (Eriksson et al 1997). Novartis is also performing clinical trials (Phase III) for the use hirudin in acute coronary syndrome. Several other indications for hirudin are being pursued such as stasis-induced venous thrombosis, diffuse microthrombosis, and hemodialysis (Markwardt 1989). Most of the potential applications of hirudin require blood levels between 80 to 3500 ng/mL (Markwardt 1989, Markwardt 1991). A potential problem with the use of injected forms of hirudin is that there are no effective antidotes for hirudin overdosing. If upon frequent injection, the wrong dose is given, there are no methods to turn the activity of hirudin off. For this reason alone, hirudin is a good candidate for transmucosal delivery via the buccal tissue. It is envisioned that the pH-sensitive mucoadhesive film-forming gel or wax-film composite containing hirudin, can easily be applied to the buccal tissue in the mouth and provide a means to safely control the dosing and dose scheduling of hirudin.

Benzodiazepines: Benzodiazepines are among the most frequently prescribed drugs in the Western world. All benzodiazepine agonists exert similar pharmacodynamic actions (e.g., activate central GABAergic neuroinhibition, thereby inducing anxiolysis, sedation/hypnosis, anticonvulsion and muscle relaxation. In turn, benzodiazepines are used for the treatment of seizures and insomnia, preoperative or procedural sedation, and for the treatment of nausea and anxiety. Most if not all of the benzodiazepine bases have little or no solubility in water and are very lipophilic (Hjortkjaer et al. 1999, Bechgaard et al. 1997). As a result, a great deal of research has gone into developing efficacious dosage forms of these drugs including; i) synthesizing water-soluble derivatives such as their hydrochloride salts, ii) developing injectable formulations of the benzodiazepine bases that do not result in precipitation of the drugs, and iii) exploring alternative routes of administration including intranasal, rectal, and buccal. Previous work has shown that intranasal doses of the benzodiazepine bases dissolved in organic solvents lead to pharmacological responses with suitable pharmacokinetic profiles. However, the repeated use of organic solvents such as ethanol, polyethylene glycol, and propylene glycol for intranasal administration is not desirable. Alternatively, benzodiazepines have been given by buccal administration with very favorable results (Schwagmeier et al. 1998; Scott et al. 1999). For example, Schwagmeier et al. showed that the maximum plasma concentration of midazolam was 55.9 ng/mL at 30 minutes following buccal administration of 5 mg midazolam with a mean bioavailability of 74.5%. Scott et al. reported that the buccal administration of 10 mg midazolam per 2 mL stopped 75% (30/40) seizures in children within an average time of 6 minutes after administration. Thus, buccal administration of benzodiazepines may be an attractive alternative to injection or intranasal administration. It is envisioned that the said pH-sensitive mucoadhesive film-forming gel or wax-film composite containing a benzodiazepine can easily be applied to the buccal tissue in the mouth and provide a means to safely and reproducibly deliver doses of the benzodiazepines for the treatment of seizures and insomnia, preoperative or procedural sedation, and for the treatment of nausea and anxiety. Benzodiazepines suitable for delivery are, but not limited to, alprazolam, camazepam, clobazam, clonazepam, desmethyldiazepam, diazepam, flunitrazepam, flurazepam, halazepam, lorazepam, lormethazepam, midazolam, nitrazepam, oxazepam, pinazepam, prazepam, triazolam, and derivatives and combinations thereof.

The term pharmaceutically acceptable means that the substance is generally regarded to be safe when used in such a manner that is widely acceptable by those skilled in the art. For reference of acceptable materials, refer to THE UNITED STATES PHARMACOEPIA.

The term pH-sensitive is defined as a substance that is affected by changes in pH so that the substance changes conformation, charge, solubility, or combinations thereof. A pH-sensitive polymer is defined as polymer that is affected by changes in pH so that the polymer changes conformation, charge, solubility, or combinations thereof. A pH-sensitive film-forming polymer is defined as polymer that is affected by changes in pH so that the polymer changes conformation, charge, solubility, or combinations thereof resulting in the precipitation, desolvation, or settling of the polymer into a film. For the purposes of this invention, it is preferred that the pH-sensitive film-forming polymers have some solubility in aqueous-based vehicles above pH 5 but limited or no solubility below pH 5. It is more preferred that the pH-sensitive film-forming polymers have some solubility in aqueous-based vehicles above pH 6 but limited or no solubility below pH 6. It is most preferred that the pH-sensitive film-forming polymers have some solubility in aqueous-based vehicles above pH 7 but limited no solubility below pH 7. Examples of pH-sensitive film-forming polymers that meet these criteria are, but not limited to, Eudragits® and cellulose acetate phthalate polymers, or derivatives thereof.

Eudragits® are synthetic cationic and anionic polymers of methacrylic acid and methacrylic acid esters in varying ratios. The polymers are generally regarded as safe and are included in the FDA Inactive Ingredients Guide (for oral capsules and tablets). The presence of positive charge (provided by the dimethylaminoethylmethacrylates), neutral charge (provided by the methacrylic acid esters) and negative charge (provided by the methacrylic acid) residues provides for interesting and useful solubility characteristics as a function of pH. In general, the cationic Eudragits are soluble at lower pHs while the anionic Eudragits are soluble at higher pHs. Neutral Eudragits usually lack aqueous solubility at any pH. For the purposes of this invention, any Eudragit polymer or derivative thereof is preferred. Even more preferred is any anionic Eudragit or derivative thereof. Most preferred is Eudragit L100-55, Eudragit L100, and Eudragit S100 or derivatives thereof. Depending on the type of Eudragit polymer selected and its solubility as function of pH, films having different properties can be prepared. Eudragit gels have been reported for the sustained-release of drugs via rectal administration (Goto et al. 1991; Kawata et al. 1991; Kim et al. 1992a; Kim et al. 1992b; Kim et al. 1992c; Umejima et al. 1993). Eudragit has also been used in buccal patches (Wong et al. 1999). Wong et al. described the use of Eudragit patches with the water-soluble cellulose-based polymers and swellable Carbopol polymers to deliver a model drug. However, for these studies Wong et al. utilized Eudragit NE40D, a neutral poly(ethylacrylate methylmethacrylate) polymer that is insoluble at all pHs (non-pH-sensitive). Eudragit has also been used to film-coat tablets for pH-dependent colon targeting after oral delivery (Khan et al. 1999). Cationic Eudragit E, which is soluble at low pH, has also been proposed for the pH-controlled drug release from mini-tablets for the treatment of inflammatory bowel disease (Leopold and Eikeler, 1998). No references or other prior art could be found that describe the use of mucoadhesive gels comprised of anionic polymers, that when applied to the skin or mucosal surfaces, form films due to effect of pH on the solubility of the anionic polymers.

Solubility refers to the extent to which a solute is dissolved in a solvent. Solubility can be described in terms such as described in REMINGTON'S PHARMACEUTICAL SCIENCES 18th edition, 1990, ranging from very soluble (less than 1 part of solvent per 1 part of solute) to insoluble (more than 10,000 parts of solvent for 1 part of solute). The term water-insoluble refers to a substance or solute where more than 10,000 parts of water are needed to dissolve 1 part of solute. A water-insoluble swellable substance refers to a substance or solute that is water-insoluble but absorbs water and swells to form a colloidal dispersion. A colloidal dispersion, as defined by REMINGTON'S "consists of at least two discrete phases", namely a solid phase and a liquid phase. The term desolvation refers to phenomena whereby a solvent such as water diffuses from a swelled substance leaving primarily one solid phase comprised of the substance. A gel is defined as a semisolid consisting of particles interpenetrated by a liquid. A gel solution is defined as a gel which has a molecule of interest dissolved in solution in the liquid phase. A gel suspension is defined as a gel which has a molecule of interest suspended in the liquid phase.

A wax refers to any water-insoluble substance composed of hydrocarbons, alcohols, fatty acids, and esters that are solids at temperatures below 40° C., but liquids at temperatures of above 40° C. Suitable waxes are, but not limited to the following, DENTSPLY® Utility Wax, beeswax, emulsifying wax, microcrystalline wax, carnauba wax, paraffin wax, white wax, yellow wax, or other suitable pharmaceutical wax. It is preferred that the wax has a melting temperature between 40° C. and 100° C., more preferred that the wax has a melting temperature between 40° C. and 80° C., and most preferred that the wax has a melting temperature between 40° C. and 65° C.

A wax-film composite refers to a bi-layer film comprised of a pH-sensitive mucoadhesive layer and a water-insoluble wax layer. A molecule of interest may be loaded in and released from either the said pH-sensitive mucoadhesive layer or said water-insoluble wax layer. It is preferred that the molecule of interest is present in the wax-film composite at a concentration of 0.001% to 20% by weight, more preferably at a concentration of 0.001% to 10% by weight, and most preferably at a concentration of 0.001% to 5% by weight. It is preferred that the pH-sensitive mucoadhesive layer is present at a concentration in the wax-film composite of 20% to 90% by weight, more preferably at 30% to 80% by weight, and most preferably at 40% to 70% by weight. Preferably, the water-insoluble wax layer is present at a concentration in the wax-film composite of 10% to 80% by weight, more preferably at 20% to 70% by weight, and most preferably at 30% to 60% by weight. For bonding the two layers of the bi-layer wax-film composite, it is preferred that the water-insoluble wax layer contain at least one water-soluble or water-swellable agents such as, but not limited to, tragacanth, polyvinyl pyrrolidone, polyvinyl alcohol, cross-linked polyacrylic acid, polyethylene glycol, a cellulose-based polymer or derivative thereof, a cross-linked polyacrylic acid polymer or derivative thereof, or other suitable pharmaceutical polymers that are water-soluble or water-swellable. Preferably, the water-soluble or water-swellable agents are present in the wax layer at a concentration of 0.05% to 10% by weight, more preferably at 1% to 8% by weight, and most preferably at 1% to 5% by weight. It is envisioned that the wax-film composite may be applied to any readily accessible topical site including, but not limited to the following; any skin surface, rectal, vaginal, nasal cavity, any location in the mouth, or other accessible topical or mucosal surfaces. A dry wax-film composite will readily adhere to the surfaces described when the surfaces are wet with saliva or other bodily fluids. However, for application to dry skin, it is envisioned that the dry wax-film composite could be easily wetted using tap water or another appropriate vehicle to promote subsequent adherence of the film to the skin. It is preferred that the wax-film composite remain adhered to the application site for at least 1 hour, more preferably for at least 75 minutes, and most preferably for at least 90 minutes.

The term mucoadhesive refers to a substance that sticks to or adheres to the skin or mucosal surfaces by forces that are measurable and by any number of mechanisms such as, but not limited to the following: hydrogen-bonding, ionic interaction, hydrophobic interaction, van der Waals interaction, or combinations thereof.

Mucosal delivery is defined as the application of a formulation or delivery system containing one or more active pharmaceuticals to a mucosal site for the purpose of eliciting a pharmacological response at the site of application or alternatively, for the active pharmaceutical to be absorbed through the mucosal membrane into the systemic circulation. Mucosal sites applicable to the application of a formulation or delivery system are, but not limited to the following, vaginal, mouth, rectal, intranasal, and the eye.

Transmucosal Delivery: Peptides, proteins, and other larger molecules are becoming increasingly more important as scientists search for new drugs to treat serious human diseases. Most often, these new larger molecules have to be injected since bioavailability by other routes is low. However, developing injectable large molecule drugs is expensive and patient compliance is often low. Researchers in the field of drug delivery have sought for decades for methods to dose larger molecules like peptides and proteins orally. However these drugs are prone to rapid and extensive degradation due to the low pH of the stomach as well as to peptidases and proteolytic enzymes throughout the gastrointestinal tract. Alternative routes have been sought such as transmucosal delivery via the lung, nose, and buccal tissue. The foreseen advantages of transmucosal delivery are; i) a faster onset of activity (i.e., achieve higher drug blood levels faster), ii) the avoidance of the first hepatic pass metabolism and the related increase of bioavailability, and iii) the avoidance of side effects related to GI absorption (Rathbone et al. 1996). However, the barriers for effective transmucosal delivery (i.e., buccal delivery) are similar to those for oral delivery. For example, the oral mucosal tissue is also characterized by a mucous layer that lines the epithelia. The mucous layer provides a substantial physical barrier as well as a chemical barrier due to the presence of a multitude of peptidases and proteolytic enzymes. In theory, delivery systems designed to adhere to this mucous layer (i.e., mucoadhesives) can serve to protect peptides from rapid and/or extensive degradation (Bodde et al. 1990; Duchene et al. 1988; Harris and Robinson 1990). The mechanism of mucoadhesion is complicated but is known to involve hydrogen bonding between the components of the delivery systems (i.e., polymers) and sialic acid residues of mucin (0.5–2.0% glycoprotein), the primary substance of mucous. The viscosity of the mucous layer is largely determined by the type and amount of the glycoproteins present. Usually, the mucous layer in the oral mucosa is about 500–600 μm thick and has a pH of 5.8–7.1. The combination of the mucous layer and the epithelial layer provides a substantial barrier for significant drug absorption. This is especially true for peptide drugs that are prone to a high degree of proteolytic degradation in the mucous layer. Further, if the peptide drugs are anionic, the negatively-charged epithelial membrane below the mucous provides a repulsive electrical "fence" of sorts.

In general, the oral transmucosal bioavailability of peptides is low (<5%), but can be increased with the use of penetration enhancers designed to disrupt the mucosal and epithelial membranes (Sayani et al. 1993; Bhatt and Johnston, 1996; Bayley et al. 1995; Bhatt and Johnston, 1997). The most often used types of penetration enhancers are surfactants (i.e., sodium lauryl sulfate), bile salts (i.e., sodium deoxycholate), and fatty acids (i.e., oleic acid). Although these penetration enhancers typically increase the absorption of peptides, the safety and long term use of these agents is of concern. Further, these penetration enhancers, by design, do not function to specifically protect peptides from proteolytic degradation in the mucosal membrane. Alternatively, a plausible strategy is to use more pharmaceutically acceptable excipients to physically protect peptides from rapid and extensive proteolytic degradation, rather than to rely on chemical means to disrupt biological membranes. For example, to enhance the transmuccosal delivery of negatively-charged peptides, the peptides may be complexed with pharmaceutically acceptable excipients that have positive charges such as, but not limited to, chitosan, polylysine, or protamine. It is thought that complexation will serve two functions; i) decrease electrostatic repulsion of the peptide drugs with the negatively-charged epithelial membrane, and ii) decrease the extent of degradation of the peptide drugs by proteolytic enzymes in the mucosal membrane.

A complex refers to the physical interaction between two substances whereby a definite stoichiometry exists. Complexation can occur by any number of mechanisms, including, but not limited to: hydrogen-bonding, ionic interaction, hydrophobic interaction, van der Waals interaction, or combinations thereof. It is envisioned that molecules of interest formulated in said delivery systems may be complexed with various pharmaceutically acceptable agents to enhance their efficacy by any number of mechanisms described above, or those still unknown.

Chitosan: Chitosan is a biodegradable polysaccharide composed of two subunits, D-glucosamine and N-acetyl-D-glucosamine linked together by $\beta(1,4)$ glycosidic bonds. When dissolved in solution, the amino groups present in the glucosamine subunits (pKa 6.5) have a positive charge (Henriksen et al. 1997; Schipper et al. 1996). Chitosan is known to be a mucoadhesive, and interacts ionically with the negatively charged sialic acid residues in mucin (Lehr et al. 1992). Chitosan has been used as a component of mucoadhesive systems (Takeuchi et al. 1996), as well as a controlled release and drug carrier systems (Berthold et al. 1993; Shiraishi et al. 1993). Chitosan has also been found to increase the nasal absorption of insulin and calcitonin (Illum et al. 1994; Aspden et al. 1996), although the mechanism by which this occurs is not clear. Finally, chitosan has been reported to form complexes with many negatively-charged molecules including indomethacin (Imai et al. 1991), sodium hyaluronate (Takayama et al. 1990), and pectin and acacia (Meshali et al. 1993). One problem that may be encountered with the use of chitosan (100 kDa) is the poor solubility of 100 kDa chitosan at neutral pH. This lack of solubility may hinder its ability to form complexes with hirudin or our ability to study the complex. A solution to this problem may be to obtain lower molecular weight chitosans (i.e., 10 kDa or 50 kDa). However, lower molecular weight chitosans are not commercially available. In our previous work with chitosan (MacLaughlin et al. 1998), we obtained lower molecular weight chitosans using a modified depolymerization technique first described by Peniston et al. (1975). This depolymerization process is a relatively simple deamination reaction where chitosan is chemically treated with sodium nitrite in 6% acetic acid at 25° C. for 1 hour. The amount of sodium nitrite used in the reaction determines the resulting chitosan molecular weight since the reaction is stoichiometric. For example, reacting 1 g of 100 kDa chitosan (Seacure 143) with 2% and 7% sodium nitrite results in final chitosan molecular weights of 50 kDa and 10 kDa, respectively. The depolymerized chitosan polymers are purified and ready to use. The molecular weight of each depolymerized chitosan polymer is determined by gel chromatography through a Beckman Ultraspherogel SEC2000 column with a 1 mL/min flow-rate of eluent 0.1M acetic acid/sodium acetate buffer containing 0.05M sodium chloride as the mobile phase.

Mucosal Vaccines: It is thought that the most effective vaccines for important viral and bacterial pathogens will require mucosal immunity since this is the site at which these pathogens infect the body (McGhee et al. 1992). However, all marketed vaccines except one (oral polio vaccine) are now administered by injectable routes and are ineffective at inducing mucosal immunity. A new promising flu vaccine (Flumist™ from Aviron) is currently being tested in phase III clinical trials. Flumist™ is administered as a nasal spray. Since the nasal associated lymphoid tissue (NALT) is part of the mucosal network, this vaccine is the first of potentially many new mucosal vaccines. Other mucosal routes are actively being pursued by researchers including the vaginal route and the mucosal regions of the gut (i.e., Peyer's patches). However, the one mucosal route that has been largely overlooked by researchers is the oral mucosal region of the mouth. This may be due to the lack of suitable delivery systems to retain and protect antigen in the mouth for an extended period of time. We hypothesize that the oral mucosa may be an ideal site for vaccination for the following reasons: i) the oral mucosa is accessible, ii) administration to the oral mucosa is needleless, and iii) the oral mucosa is a preferred site for antigen presentation. Vaccination without the use of needles would provide a distinct advantage in terms of both cost and safety over conventional vaccines that must be given with needles. The oral mucosa is theoretically a preferred site for antigen presentation since in the normal course of a day our bodies are exposed to hundreds of antigens during eating and other hand-to-mouth activities. In most cases, the oral mucosal tissue, which comprises a high density of Langerhans cells, and T-lymphocytes as well as the mucosal associated lymphoid tissue (MALT), is our first line of defense against both viral and bacterial pathogens. The percentage of Langerhan cells in the oral mucosa, about 4% of the total cells, is comparable to the percentage of Langerhan cells found in the skin epidermis. Langerhan cells are immature dendritic cells that are thought to be the most potent antigen presenting cell type. However, the oral mucosa has about a 40-fold increase in the number of T-lymphocytes as compared to the skin. The presence of Langerhan cells and T-lymphocytes along with MALT tissue (i.e., tonsils, salivary glands, Waldeyer's Ring, and the pharyngeal lymphoid tissue) makes the oral mucosa a theoretically potent immunization site. For example, unlike vaccination by the skin, intravenous, subcutaneous, and muscle routes, vaccination via the oral mucosa route may result in both cellular and mucosal (humoral) immune responses. Finally, vaccination by the oral mucosa route to target the MALT remains a relatively untested strategy as compared to previous efforts to target the nasal-associated lymphoid tissues (NALT) or the gut-associated lymphoid tissue (GALT). One explanation for the lack of published results on vaccination by the oral mucosa route is the lack of suitable pharmaceutical formulations to retain and stabilize antigens at the site for a suitable length of time.

Oral Mucosal Delivery and Vaccination: Many reports in the literature have described the use of polymeric delivery systems to deliver drugs locally in the mouth or transmucosally into the systemic circulation. See Leung et al. (1991) for a review on delivery systems for the oral mucosa. However, to our knowledge no group has reported on the use of such delivery systems to deliver antigens, specifically DNA plasmids expressing antigens, in the oral mucosa. Two recent published studies have investigated the application of antigens alone (with no delivery systems) to the oral mucosa route for immunization. Etchart et al. (1997) showed that the use of a DNA plasmid encoding measles virus hemoagglutinin (HA) injected into the buccal mucosa of mice induced HA-specific cytotoxic-T-lymphocyte (CTL) responses. The CTL responses to expressed HA after DNA plasmid was applied to the buccal mucosa were much stronger than those responses after oral or intrajejunal immunization suggesting the feasibility of the oral mucosa as a route of immunization. Also, Casetta and Negretti (1998) demonstrated that antigenic mixtures of several bacteria could induce specific salivary IgA after rubbing the mixtures on the rat gingival mucosa. These publications demonstrate the potential utility of the oral mucosa as a route of immunization for both genetic vaccines (i.e., DNA plasmids expressing antigens) and subunit (protein antigen) approaches.

Genetic Vaccines: After the concept of genetic immunization was first demonstrated by Johnston's group in 1992 (Tang et al., 1992), numerous studies have reported the potential prophylactic and therapeutic use of genetic vaccines for combating various infectious diseases (Taubes, 1997; Ulmer et al., 1996; Robinson and Torres, 1997; Liu et al., 1995). Vaccines of this composition appear to be both efficacious in the short term and able to elicit a prolonged anamnestic response, which is capable of preventing or resolving infection when challenged up to one year after vaccination (Yankauckas et al., 1993). Genetic vaccines elicit a broader immune response than do subunit vaccines. They induce both cellular and humoral responses that are reminiscent of attenuated and whole-killed viral vaccines. Further, genetic vaccines can be prepared with relative ease of synthesis and production. Expression plasmids can be generated quickly once the antigen's coding sequence is known and small- and large-scale DNA purification methods are well established. Genetic vaccines also avoid some of the safety concerns of conventional vaccines in that there is no chance of disease due to co-purification of contaminating virus or reversion of the attenuated strain in the patient.

Vaginal Delivery: Many types of dosage forms have been proposed for the vaginal delivery of drugs including gels, creams, suppositories, films, foams, and tablets. In designing a dosage form intended for vaginal application, one must consider multiple parameters including, but not limited to, i) the physico-chemical properties of the drug (i.e., solubility, stability, etc.), ii) the intended duration of action or activity, iii) the context in which the dosage form is used, and iv) patient preferences. For example, clinical studies have shown that a majority of women prefer a gel to a cream formulation and both of these over the other dosage forms listed above (Hardy et al. 1998a). Women also prefer a dosage form that has no odor or a pleasant mild odor and also one that has no color (Hardy et al. 1998b). The gel formulations will be able to be applied manually or by use of a simple applicator. Importantly for use a microbicidal agents, the applied gel formulations will be able to cover a large area of the mucosal tissue, adhere to the tissue, and potentially provide prolonged pharmacological activity of the molecule of interest.

A plethora of different mucoadhesive gel formulations have been described in the literature and several are now marketed products. Typically, the mucoadhesive component of the formulation is a biocompatible polymer, such as polyacrylic acid that is cross-linked with an acceptable agent to create an insoluble gel. The use of an insoluble gel is desirable since it remains in contact with the mucosal tissue for much longer periods of time. Cross-linked polyacrylic acid polymers, such as NOVEON and CARBOMER, have been shown to stay attached to the mucosal lining in the vagina for up to three to five days (March and Nakamura, 1993). Further, gels containing NOVEON and/or CARBOMER have been used as vaginal lubricants so it is envisioned that the described gels may be used during sexual intercourse. NOVEON and CARBOMER-based polymers are weak acids and contain many negatively-charged carboxyl-groups. The multiple negative charges on these polymers promote hydrogen-bonding between the polymers and the negatively charged mucin, the main glycoprotein that allows for the attachment of mucus to the epithelial lining of the vaginal wall (Park and Robinson, 1985). NOVEON and CARBOMER-based polymers have been shown to have maximum hydrogen-bonding in the pH range of 4.0 to 6.0. This is ideal for use in the vagina which has a normal pH value of about 4.5 (Stevens-Simon et al., 1994; Garcia-Closas, et al., 1999). It is envisioned that gels comprised of pH-sensitive polymers and water-insoluble mucoadhesive polymers such as NOVEON and CARBOMER may provide superior delivery of molecules of interest to the vagina since the lower pH of the vagina will cause the pH-sensitive polymer to form a long lasting film to retain and/or deliver the molecule of interest in a more efficacious manner.

The following Examples are described to illustrate the different aspects of the invention. These Examples should not be used in any way to limit the scope of the invention.

EXAMPLES

Materials: Recombinant hirudin and bovine α-thrombin are from Sigma Chemicals (St. Louis, Mo.). Chromozym-TH is from Boehringer Mannheim. Chitosan Seacure 143 (85–90% deacetylated) is from Natural Biopolymer Inc. (Raymond, Wash.). All EUDRAGIT polymers were obtained from Rohm America, Inc. (Piscataway, N.J.). NOVEON and CARBOMERs were obtained from BF Goodrich (Cleveland, Ohio). Glycerin, polyethylene glycol 400, isopropyl myristate, ethanol, sodium hydroxide, and propylene glycol were all of USP/NF grade and were purchased from Spectrum Quality Products, Inc. (New Brunswick, N.J.). PicoGreen dsDNA Quantitation Kit was purchased from Molecular Probes, Inc. (Eugene, Oreg.). DENTSPLY® Utility Wax was obtained from DENTSPLY International (York, Pa.).

Example 1

A placebo pH-sensitive mucoadhesive film-forming gel was made as follows. Water (44.1 % w/w) was added to a 250 mL stainless steel beaker and stirring was begun at 200 rpm using a Caframo Stirrer. NOVEON (0.5% w/w) and CARBOMER 971 (0.8% w/w) were added very slowly to the stirring water until the solution was clear and viscous with no visible solid material in solution. Glycerin (50.4% w/w) was then added to the polymers in water. EUDRAGIT L100 (2.0% w/w) was added and the solution and the viscous solution became slightly milky in color and less viscous. 18% sodium hydroxide (2.2% w/w) was then added and the whitish gel became viscous. The pH of the placebo gel was measured by taking 1 mL of the gel and dispersing it into 5 mL water and measuring the pH after 1 hour. The pH of the gel was 6.3±0.02 (n=3). When the placebo gel was spread onto the skin of a human volunteer's hand; it produced a clear film. Placebo gel stored under controlled conditions at 25° C./60% Relative Humidity for 1 week and 1 month had pH of 6.2±0.07 (n=3) and 6.2±0.06 (n=3), respectively. Placebo gel stored under controlled conditions at 40° C./75% Relative Humidity for 1 week and 1 month had pH of 6.1±0.03 (n=3) and 6.1±0.09 (n=3), respectively. These results demonstrated that the placebo gel was stable when stored under the conditions tested.

Example 2

A 5% triclosan pH-sensitive mucoadhesive film-forming gel suspension was made as follows. Water (39.0% w/w) was added to a 250 mL stainless steel beaker and stirring was begun at 200 rpm using a Caframo Stirrer. Noveon (0.5% w/w) and Carbomer 971 (0.65% w/w) were added very slowly to the stirring water until the solution was clear and viscous with no visible solid material in solution. Glycerin (50.6 g) was then added to the polymers in water. Eudragit L100 (2.0% w/w) was added and the solution and the viscous solution became slightly milky in color and less viscous. 18% sodium hydroxide (2.4% w/w) was then added and the whitish gel became viscous. Triclosan (5.0% w/w) was then added to produce a homogenous whitish gel suspension. The pH of the 5% triclosan gel was measured by taking 1 mL of the gel and dispersing it into 5 mL water and measuring the pH after 1 hour. The pH of the gel was 6.5±0.1 (n=3). When the 5% triclosan gel was spread onto the skin of a human volunteer's hand, it produced a clear film. The 5% triclosan gel was stored under controlled conditions at 25° C./60% Relative Humidity for 1 week and 1 month had pH of 6.5±0.1 (n=3) and 6.4±0.1 (n=3), respectively. 5% triclosan gel stored under controlled conditions at 40° C./75% Relative Humidity for 1 week and 1 month had pH of 6.3±0.02 (n=3) and 6.2±0.1 (n=3), respectively. These results demonstrated that the 5% triclosan gel was stable when stored under the conditions tested.

Example 3

A 1% triclosan pH-sensitive mucoadhesive film-forming gel solution was made as follows. Propylene glycol (37.6% w/w) was added to a 250 mL stainless steel beaker and stirring was begun at 200 rpm using a Caframo Stirrer. Triclosan (1.0% w/w) was added to the stirring propylene glycol to produce a clear semi-viscous solution. Eudragit L100 (0.2% w/w) was then added to the solution. Polyethylene glycol 400 (30.8% w/w) was then added followed by 3 mM phosphate buffer, pH 8 (28.9% w/w). To the clear semi-viscous solution, Noveon (1.0% w/w) and Carbomer 971 (0.5% w/w) were added very slowly. After additional mixing for 2 hours, the final 1% triclosan gel was a very slightly opaque gel solution. When the 1% triclosan gel solution was spread onto the skin of a human volunteer's hand; it produced a clear film.

Example 4

A placebo pH-sensitive mucoadhesive film-forming gel was made as follows. Water (94.2% w/w) was added to a 250 mL stainless steel beaker and stirring was begun at 200 rpm using a Caframo Stirrer. Noveon (1.0% w/w) and Carbomer 971 (0.5% w/w) were added very slowly to the stirring water until the solution was clear and viscous with no visible solid material in solution. Eudragit L100 (2.0% w/w) was added and the solution and the viscous solution became slightly milky in color and less viscous. 18% sodium hydroxide (1.2% w/w) was then added and the whitish gel became viscous. Propylene glycol (0.5% w/w) and polyethylene glycol 400 (0.6% w/w) were added to the viscous gel. The final placebo formulation was a white viscous gel. However, when the placebo gel was spread onto the skin of a human volunteer's hand, it produced a clear film.

Example 5

A 5% amlexanox pH-sensitive mucoadhesive film-forming gel suspension was made as follows. Water (63.5% w/w) was added to a 250 mL glass jar and stirring was begun at 1100 rpm using a Caframo Stirrer. Carbomer 971 (0.5% w/w) was added to the stirring water and mixed until fully hydrated. Next, Noveon (1.0% w/w) was added to the clear viscous solution and mixed until fully hydrated. Glycerin (1.0% w/w) was then added followed by ethanol (21.0% w/w). To the clear viscous gel, Eudragit L100 (7.0% w/w) was added to produce a whitish gel. Amlexanox (5.0% w/w) was then added and stirring was continued to result in a homogenous suspension of Amlexanox in the viscous gel. Finally, 18% sodium hydroxide (1.0% w/w) was added to adjust the pH. The final formulation was a whitish gel suspension. When the 5% Amlexanox gel suspension was applied to the buccal region of a human volunteer's mouth, a whitish thin film formed within 20 seconds.

Example 6

A 1.5% amlexanox pH-sensitive mucoadhesive film-forming gel solution was made as follows. A 50 mM glycine/sodium hydroxide buffer, pH 9.0 ((75% w/w), 95% ethanol (7.4% w/w), and glycerin (1.0% w/w) were added to a 250 mL glass jar and stirring was begun at 200 rpm using a Caframo Stirrer. Noveon (1.0% w/w) was then added to the solution and mixed at 800 rpm until fully hydrated. Carbomer 971 (1.0% w/w) was then added to the viscous gel and mixed at 800 rpm until fully hydrated. To the clear viscous gel, Eudragit L100 (0.1% w/w) was added to produce a whitish gel. A volume of approximately 7 mL 2N sodium hydroxide was added slowly to raise the pH to 8.8. At this pH, the formulation was a clear and viscous gel. Amlexanox was then added slowly in 0.25 g increments causing the pH of the whitish gel to drop to between pH 7.0 and 7.5. After each addition of Amlexanox, approximately 0.75 mL to 1.0 mL of 2N sodium hydroxide was needed to raise the pH to 8.8 at which time the gel became clear. The final concentration of Amlexanox was 1.5% w/w and the total amount of 2N sodium hydroxide added was 12 mL (13% w/w). The final formulation was a clear and viscous gel. When the 1.5% Amlexanox gel solution was spread onto the skin of a human volunteer's hand, it produced a clear film.

Example 7

Preparation of initial wax-film composites using different waxes. A gel of Noveon (2%) and Eudragit S100 (0.5%) in ethanol was casted on a plastic circular hollow ring (diameter=2.357 inches) fixed on Mylar film and dried in a 55° C. oven to form homogenous mucoadhesive films having a diameter of 2.357 inches. Several ¼ inch disks were cut using a punch. The disks were dipped into the following melted wax compositions to form a homogeneous coating on one side of the pH-sensitive mucoadhesive films: beeswax, emulsifying wax, and DENTSPLY® Utility Wax. The results showed that the dried beeswax and emulsifying wax layers peeled away from the mucoadhesive layer over 30 minutes. The DENTSPLY® Utility Wax exhibited a very slight tendency to peel away but was mostly adhered. In an effort to mold the two layers of the wax-film composites more efficiently, a water-swellable polymer, tragacanth, was dispersed into melted DENTSPLY® Utility Wax at a concentration of either 1% w/w, 7% w/w, and 10% w/w. Mucoadhesive disks were then dipped into the new melted wax compositions to form a homogeneous coating on one side of the mucoadhesive films. The results showed that the two layers, mucoadhesive layer and wax layer with 1% tragacanth, were permanently molded together when stored at ambient conditions. Wax-film composites made with either 7% w/w or 10% w/w tragacanth in the wax layer caused the wax to be too permeable to water.

Example 8

Six different pH-sensitive mucoadhesive wax-film composites were made using six different Noveon and Eudragit S100 compositions in ethanol as shown in Table 1 below. A specific volume of each gel was added to a plastic circular hollow ring (diameter=2.357 inches) fixed on Mylar film to result in 450–480 mg total polymer in the ring.

TABLE 1

Preparation of Wax-Film Composites Having Different Ratios of Noveon/Eudragit S100 in the pH-Sensitive Mucoadhesive Layer

| Gel # | Noveon (%) in gel | Eudragit (%) in gel | Volume of Gel Added to Ring (mL) | Noveon (mg) in Dried Film | Eudragit (mg) in Dried Film | Ratio of Noveon/Eudragit in pH-sensitive mucoadhesive Wax-film composite |
|---|---|---|---|---|---|---|
| 1 | 1 | 2 | 15 | 150 | 300 | 1:2 |
| 2 | 2 | 2 | 12 | 240 | 240 | 2:2 |
| 3 | 2 | 1 | 15 | 300 | 150 | 2:1 |
| 4 | 1 | 0.5 | 30 | 300 | 150 | 2:1 |
| 5 | 2 | 0.67 | 12 | 240 | 113.9 | 3:1 |
| 6 | 2 | 0.5 | 18.5 | 370 | 92.5 | 4:1 |

The ethanol from each Gel 1–6 was evaporated in a 55° C. oven to form homogeneous films (Films 1–6) of having a diameter of 2.357 inches. The dry Films 1–6 still on the Mylar film were dipped in melted DENTSPLY® Utility Wax (containing 1% w/w tragacanth polymer) at 55° C. resulting in a homogenous coating of a wax layer on one side of the pH-sensitive mucoadhesive wax-film composites 1–6. Three-¼ inch disks each of the wax-film composites 1–6 for were made using a ¼ inch punch. Exactly 6 µL of a 40 mM KH$_2$PO$_4$/NaOH Buffer, pH 6 was added to the mucoadhesive side of the ¼ inch wax-film composites 1–6 (n=3) and the disks were fixed to glass microscope cover-slips (to simulate the negatively-charged mucosal surface). The disks were allowed to dry for 4 hours at room temperature and then each cover-slip containing adhered disk was placed in a bath of 40 mM KH$_2$PO$_4$/NaOH Buffer, pH 6 at 37° C. (unstirred). The time at which each disk dislodged from the cover-slip was recorded and the results of the study are plotted in FIG. 2. The data demonstrated that when the amount of total polymer per ¼ inch disk was held constant, the weight ratio of each Noveon and Eudragit S100 polymers used in the pH-sensitive mucoadhesive layer significantly affected the adhesive time on the glass.

Example 9

Five different pH-sensitive mucoadhesive wax-film composites were made using the same ethanol-based gel containing 2% Noveon and 0.67% Eudragit S100. The purpose of this experiment was to test the effect of having different amounts of total polymer in the mucoadhesive layer on the total adherence time of wax-film composites to glass. A specific volume of the gel was added to a plastic circular hollow ring (diameter=2.375 inches) fixed on Mylar film to result in different amounts of total polymer as shown in Table 2 below.

TABLE 2

Preparation of Wax-Film Composites Having Different Total Polymer Contents (Noveon/Eudragit S100) in the pH-Sensitive Mucoadhesive Layer

| Sample | Noveon (%) in gel | Eudragit (%) in gel | Volume of Gel Added to Ring (mL) | Total Amount of Polymer in pH-sensitive mucoadhesive Wax-film composite (mg) |
|---|---|---|---|---|
| 1 | 2 | 0.67 | 4 | 1.2 |
| 2 | 2 | 0.67 | 11 | 3.3 |
| 3 | 2 | 0.67 | 19 | 5.6 |
| 4 | 2 | 0.67 | 31 | 9.2 |
| 5 | 2 | 0.67 | 38 | 11.2 |

Figure 3:
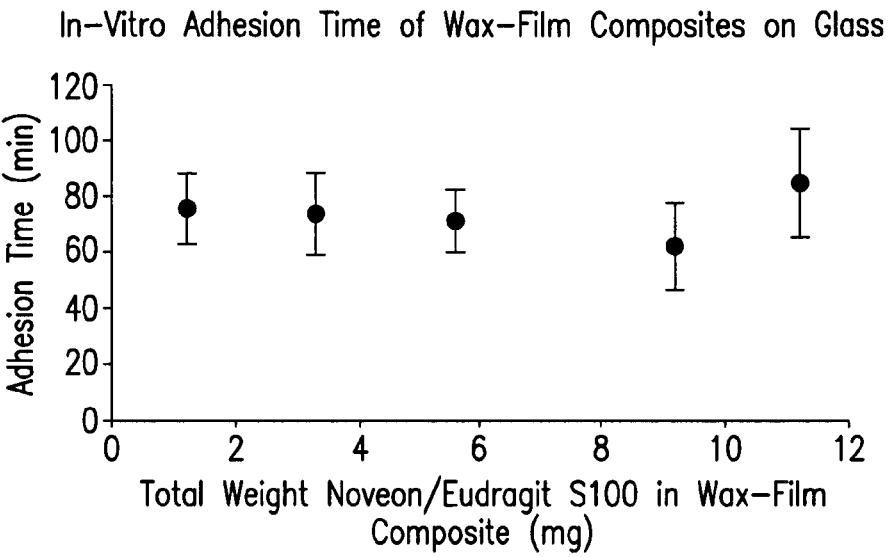
FIG. 3 shows in vitro adhesion time of ¼ inch wax-film composites (n=3 each) on glass submerged in 40 mM $KH_2PO_4$/NaOH buffer, pH 6 at 37° C. (stirred at 100 rpms). Each mucoadhesive layer contains from 1.2 mg to 11.2 mg of total polymer comprised of NOVEON and EUDRAGIT S100 in a weight ratio of 3:1. The wax layer consists of DENTSPLY® Utility Wax containing 1% w/w tragacanth polymer. See Table 2 and Example 9 for additional details.

The ethanol from each Samples 1–5 was evaporated in a 55° C. oven to form homogenous films (Films 1–5) having a diameter of 2.375 inches. The dry Films 1–5 still on the Mylar film were dipped in melted DENTSPLY® Utility Wax (containing 1% w/w tragacanth polymer) at 55° C. resulting in a homogenous coating of the pH-sensitive mucoadhesive wax-film composites 1–5. Three-¼ inch disks each of the wax-film composites 1–5 for were made using a ¼ inch paper punch. Exactly 6 µL of a 40 mM $KH_2PO_4$/NaOH Buffer, pH 6 was added to the mucoadhesive side of the ¼ inch wax-film composites 1–6 (n=3) and the disks were fixed to glass microscope cover-slips (to simulate the negatively-charged mucosal surface). The disks were allowed to dry for 4 hours at room temperature and then each cover-slip containing adhered disk was placed in a bath of 40 mM $KH_2PO_4$/NaOH Buffer, pH 6 at 37° C. (stirred at 100 rpms). The time at which each disk dislodged from the cover-slip was recorded and the results of the study are plotted in FIG. 3. The data demonstrated that when the amount of total polymer per ¼ inch disk was increased, there was no effect on the adhesive time on the glass. This result was most likely due to the fact that both the glass and the wax layer are impermeable to the buffer. It is expected that if the wax-film composites as described in this Example were placed on a permeable substrate such as a membrane or the buccal tissue, differences in the adhesion time would be observed.

Example 10

Pre-loading and post-loading of plasmid DNA into pH-sensitive mucoadhesive wax-film composites was carried out. Plasmid DNA (CMV-luciferase plasmid) was loaded into the wax-film composites during the manufacturing process or post-loaded onto pre-made composites. An ethanol-based gel containing 3% Noveon and 1% Eudragit S-100 was prepared. For pre-loaded composites, 12.6 g of the gel was diluted with 6.3 g ethanol and 400 µL of plasmid DNA (920 µg) was added. For post-loaded composites, 12.6 g of the gel was diluted with 6.3 g ethanol. Each gel was added to a plastic circular hollow ring (diameter=2.375 inches) fixed on Mylar film. The ethanol from each gel was evaporated in a 55° C. oven to form homogenous films (Pre-loaded and Post-Loaded) having a diameter of 2.375 inches. The dry Pre-loaded and Post-Loaded Films, still on the Mylar film, were dipped in melted DENTSPLY® Utility Wax (containing 1% w/w tragacanth polymer) at 55° C. resulting in a homogenous coating of the pH-sensitive mucoadhesive wax-film composites. Three ¼ inch disks each of the wax-film composites were made using a ¼ inch paper punch. Pre-loaded wax-film composites contained 10 µg plasmid DNA per ¼ inch disks. To Post-loaded wax-film composites, exactly 4.3 µL of plasmid DNA (10 µg) was added to the mucoadhesive layer and allowed to dry for 4 hours.

Figure 4:
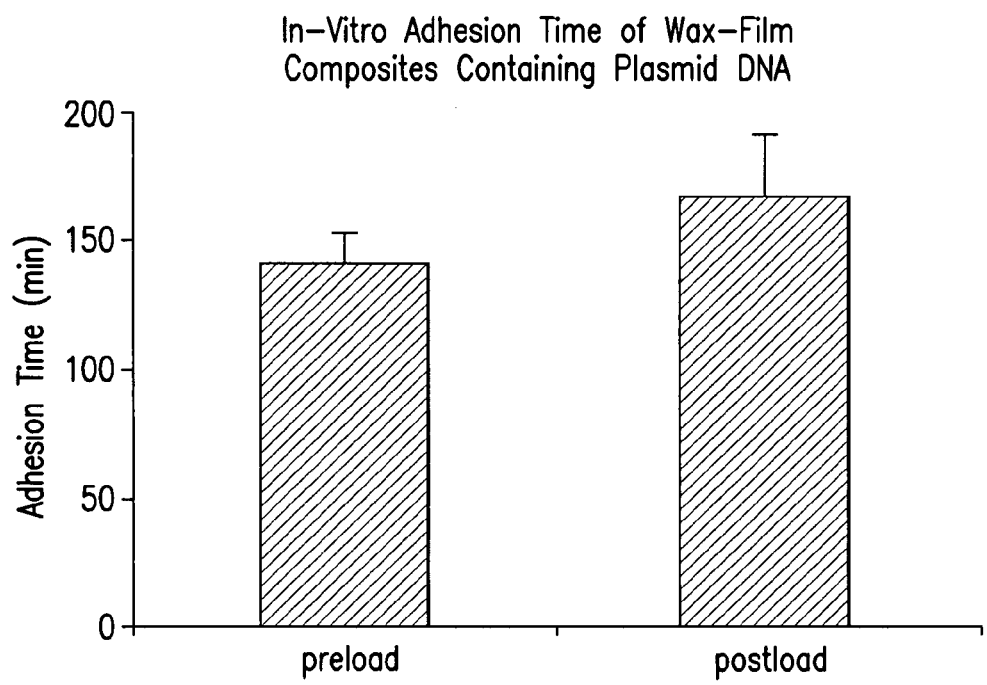
FIG. 4 shows in vitro adhesion time of ¼ inch wax-film composites containing plasmid DNA (10 µg) either incorporated during the manufacturing process ('preload') or aliquoted onto the mucoadhesive layer after the manufacturing process ('postload'). Wax-film composites (n=5 each) were adhered to glass and submerged in 40 mM $KH_2PO_4$/NaOH buffer, pH 6 at 37° C. (unstirred). See Example 10 for additional details.

Adhesion Time: To dry wax-film composites containing plasmid DNA (pre-loaded and post-loaded) exactly 6 µL of a 40 mM $KH_2PO_4$/NaOH Buffer, pH 6 was added to the mucoadhesive side of the ¼ inch wax-film composites (n=3 for both Pre-loaded and Post-loaded) and the disks were fixed to the inside of a 300 mL glass beaker (to simulate the negatively-charged mucosal surface). The disks were allowed to dry for 4 hours at room temperature and then submerged in 40 mM $KH_2PO_4$/NaOH Buffer, pH 6 at 37° C. (stirred at 100 rpms). The time at which each disk dislodged from the glass was recorded and the results of the study are plotted in FIG. 4. The data demonstrated that pre-loading or post-loading plasmid DNA had no effect on the adhesion times of the wax-film composites to glass.

Figure 5:
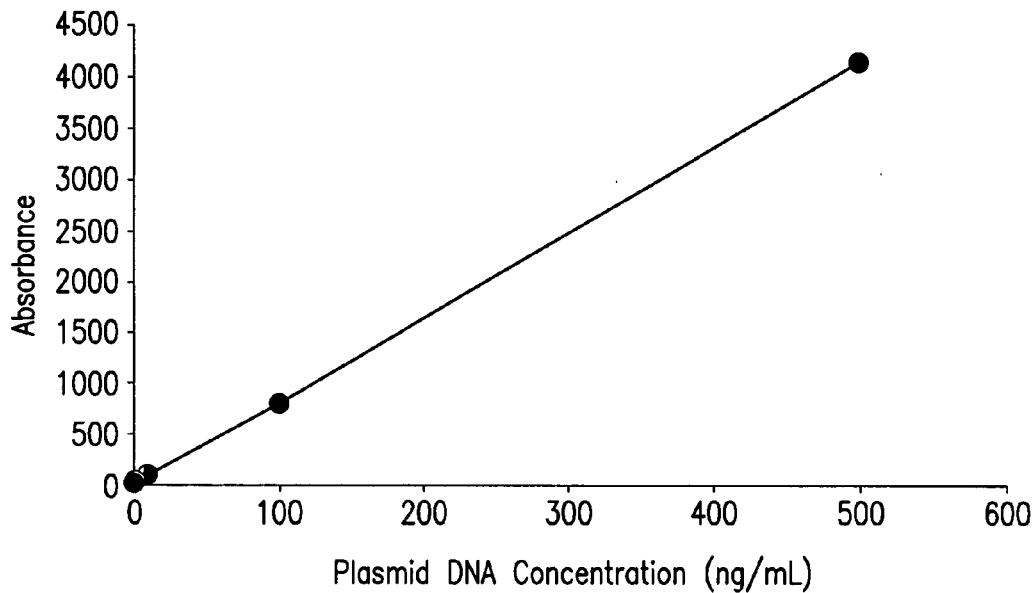
FIG. 5 shows a standard curve for plasmid DNA in solution as measured by the PicoGreen DNA Quantitation Kit (from Molecular Probes, Inc., Eugene, Oreg.).

Quantitation of Plasmid DNA: Plasmid DNA in solution was quantified using the PicoGreen dsDNA Quantitation Kit. In brief, Phage Lamda DNA was diluted with TE (Tris-EDTA) buffer (pH=7.5) to obtain a DNA concentration of 0, 2, 20, 100, and 1000 ng/mL. These solutions were further diluted twice with PicoGreen containing TE buffer. One mL of the solution was measured by the fluorescence spectrophotometer (Hitachi Instrument, Inc., Fairfield, Ohio) to obtain a standard plasmid DNA calibration curve as shown in FIG. 5. This curve was used for calibration of the concentration of unformulated plasmid DNA and plasmid DNA released from wax-film composites.

Figure 6:
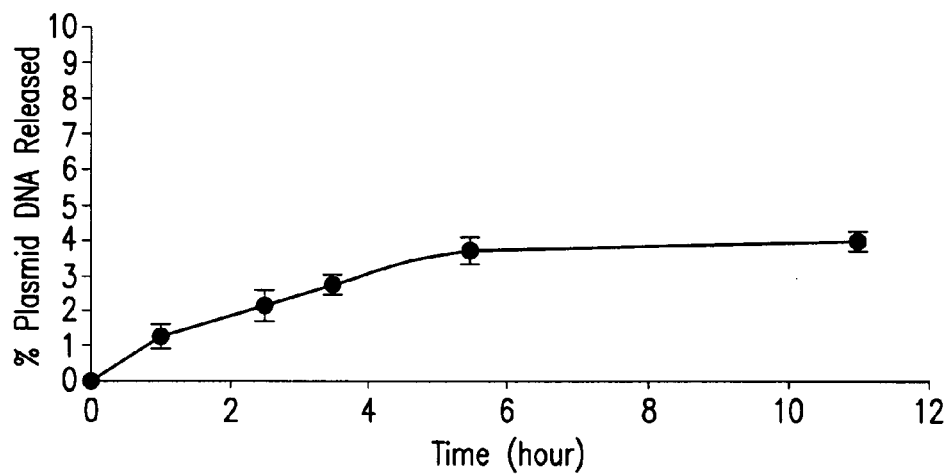
FIG. 6 shows the release of plasmid DNA pre-loaded into wax-film composites. Wax-film composites were made as described in Example 10 using a mucoadhesive gel comprised of NOVEON/EUDRAGIT S100 (3:1 w/w) and plasmid DNA. The wax layer consists of DENTSPLY® Utility Wax containing 1% w/w tragacanth polymer. Five ¼ inch wax-film composites containing of plasmid DNA (5 μg) were submerged separately into 1 mL 10 mM PBS buffer, pH 7.4 at 37° C. At various times, exactly 100 μL solution was aliquoted for DNA quantitation using the PicoGreen DNA Quantitation Kit. Exactly 100 μL fresh PBS was added to replace the removed volume at each time point.
Figure 7:
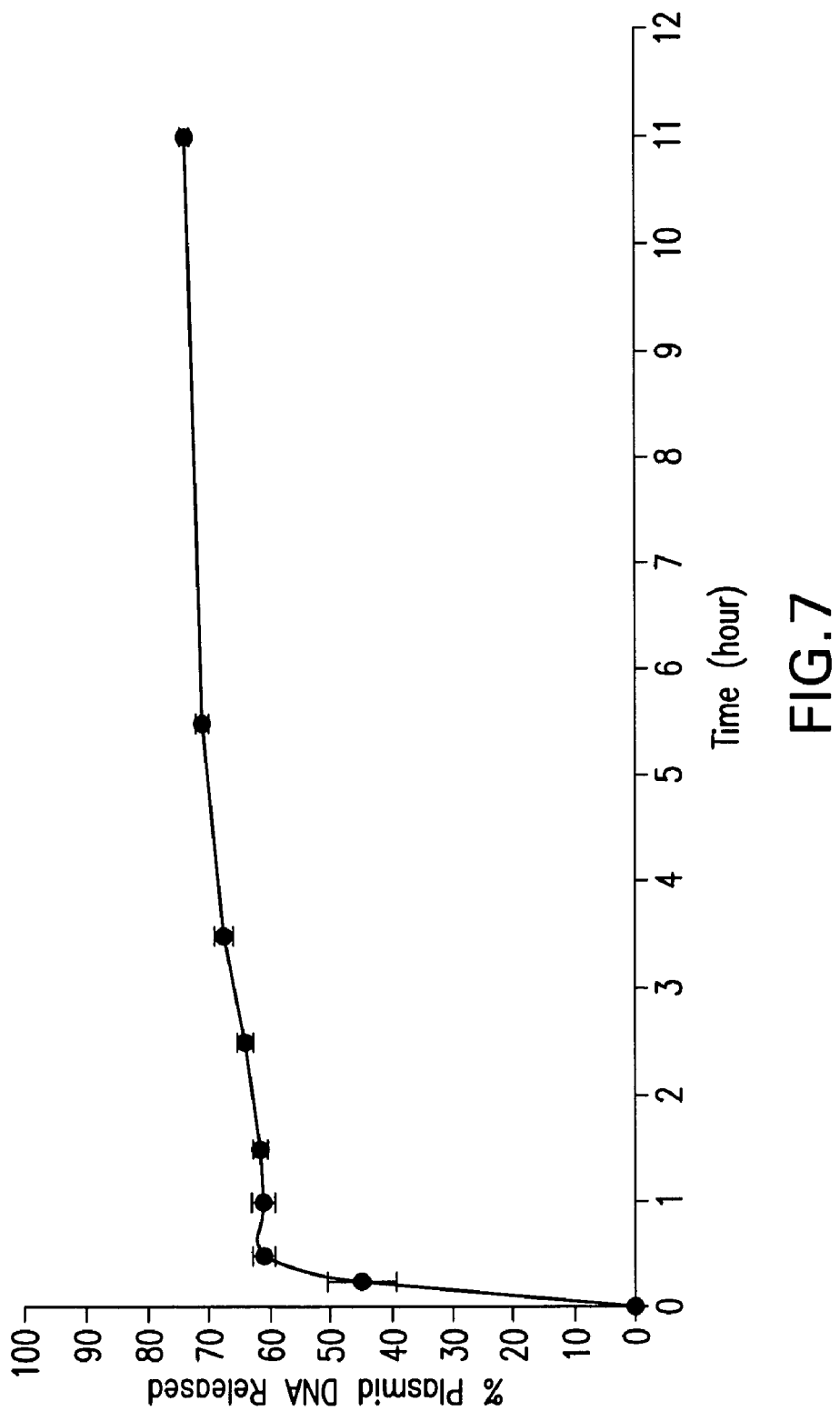
FIG. 7 shows the release of plasmid DNA post-loaded into wax-film composites. Wax-film composites were made as described in Example 10 using a mucoadhesive gel comprised of NOVEON/EUDRAGIT S100 (3:1 w/w). The wax layer consists of DENTSPLY® Utility Wax containing 1% w/w tragacanth polymer. Plasmid DNA (5 μg) was added to five individual ¼ inch wax-film composites, allowed to air dry for 4 hours, and then submerged separately into 1 mL 10 mM PBS buffer, pH 7.4 at 37° C. At various times, exactly 100 μL solution was aliquoted for DNA quantitation using the PicoGreen DNA Quantitation Kit. Exactly 100 μL fresh PBS was added to replace the removed volume at each time point.

In-Vitro Release of Plasmid DNA from Wax-Film Composites: Five ¼ inch wax-film composites containing of plasmid DNA (5 µg) (pre-loaded and post-loaded) were submerged separately into 1 mL 10 mM PBS buffer, pH 7.4 at 37° C. At various times, exactly 100 µL solution was aliquoted for DNA quantitation using the PicoGreen DNA Quantitation Kit. Exactly 100 µL fresh PBS was added to replace the removed volume at each time point. As shown in FIG. 6, the release rate of plasmid DNA pre-loaded into wax-film composites was low as only about 4% of the total amount of plasmid DNA loaded into the wax-film composites during the manufacturing process was released in 11 hours. This result may be explained by the time needed for a large molecule such as plasmid DNA to diffuse through the mucoadhesive layer of Noveon and Eudragit S100. In comparison, the release rate of plasmid DNA post-loaded onto wax-film composites was much more rapid, as approximately 60% of the plasmid DNA was released within 1 hour (see FIG. 7). These results demonstrate that plasmid DNA may be either pre-loaded or post-loaded on wax-film composites and released at different rates as necessary. A wax-film composites containing either pre-loaded or post-loaded plasmid DNA expressing a relevant peptide or protein antigen can be placed in the mouth of a warm-blooded mammal to elicit a measurable and protective immune response.

Example 11

Hirudin was both pre-loaded and post-loaded into wax-film composites in a similar manner as described in Example 10. The release rate of hirudin (0.5 mg) from ¼ inch wax-film wax-film composites was measured using both a HPLC assay and a chromogenic substrate assay.

Chromogenic Substrate Assay for Hirudin: This anti-amidolytic assay was first reported by Spannagl et al. (1991). It can be used to both quantitate hirudin in solution and determine its retained stability/functionality (i.e., ability to inhibit thrombin-catalyzed digestion of the synthetic substrate).

Figure 8A:
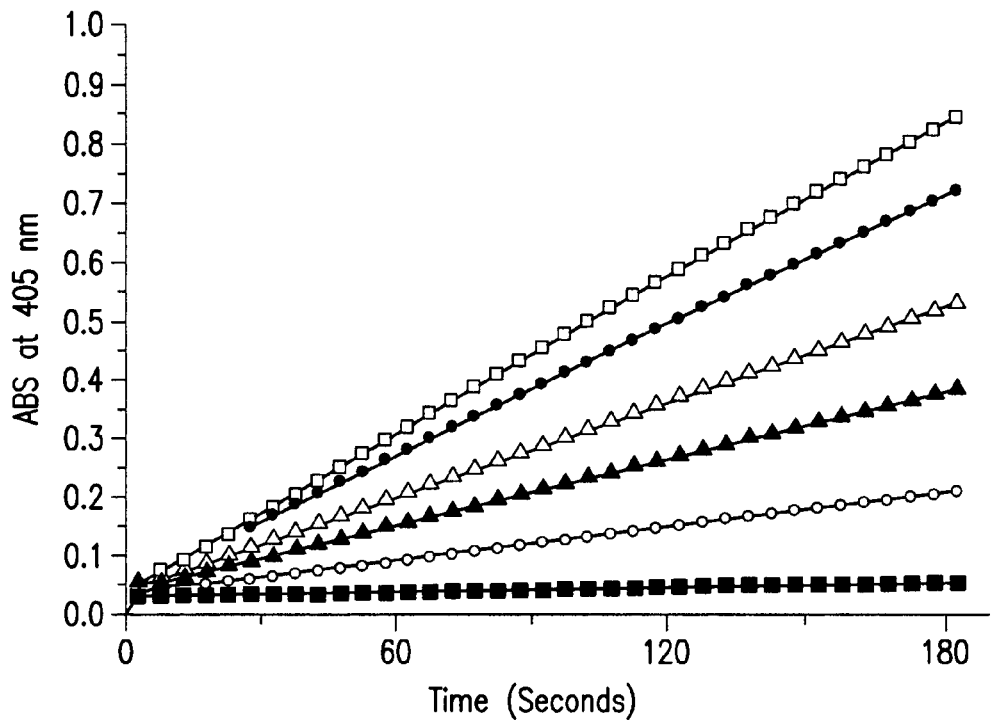
FIG. 8 shows: (A) The reaction kinetics of Chromozym-TH and uncomplexed thrombin. Hirudin was added to excess thrombin and residual uncomplexed thrombin was assayed spectroscopically after the addition of Chromozym-TH. Hirudin was added to the 1.0 ml volume in the following amounts: 0 ng (□), 16.9 ng (●), 33.8 ng (Δ), 50.7 ng (▲), 67.6 ng (○), and 84.4 ng (■). (B) Calibration curve for released hirudin in solution. The figure was made by plotting the difference between the thrombin base value absorbance (thrombin in the presence of substrate only) and the hirudin sample values versus the concentration of hirudin standards from A.
Figure 8B:
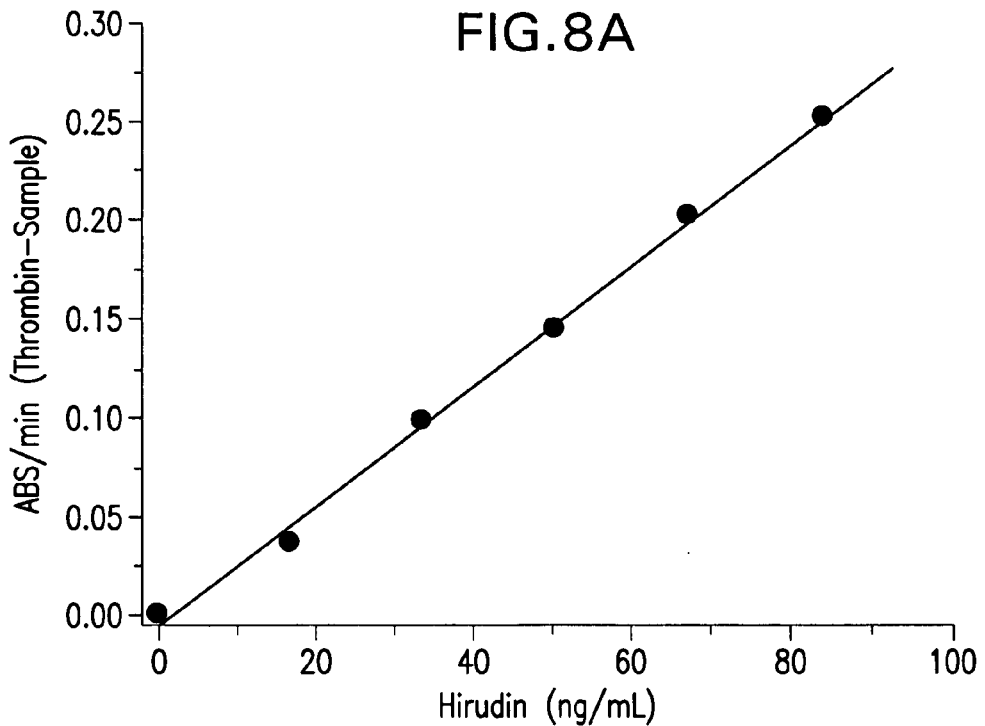

Samples of hirudin (500 uL) were mixed with 400 uL of reagent mixture consisting of 67 mM Tris-HCl buffer, pH 8.0, containing 133 mM NaCl and 0.1% Polyethylene glycol (Mw 8000) and 1 nM of bovine α-thrombin. Hirudin and thrombin were allowed to form a complex at room temperature for 2 minutes. After 2 minutes, 100 uL of the 200 uM synthetic substrate (Tos-Gly-Pro-Arg-pNA; Chromozym-TH from Boehringer-Mannheim) was added and the digestion of the substrate pNA (para-nitroaniline) was monitored at 405 nm for 3 minutes. As shown in FIG. 8A, the reactions proceeded linearly for 3 minutes. The addition of different amounts of hirudin in the reaction resulted in different slopes. A slope of ~0 signifies complete inhibition of thrombin-catalyzed digestion of the substrate. Complete inhibition theoretically occurs when the mole ratio of hirudin to thrombin is 1. A calibration curve for released hirudin (see FIG. 8B) in solution was made by plotting the difference between the thrombin base value absorbance (thrombin in the presence of substrate only) and the hirudin sample values versus the concentration of hirudin standards from FIG. 8A.

Figure 9:
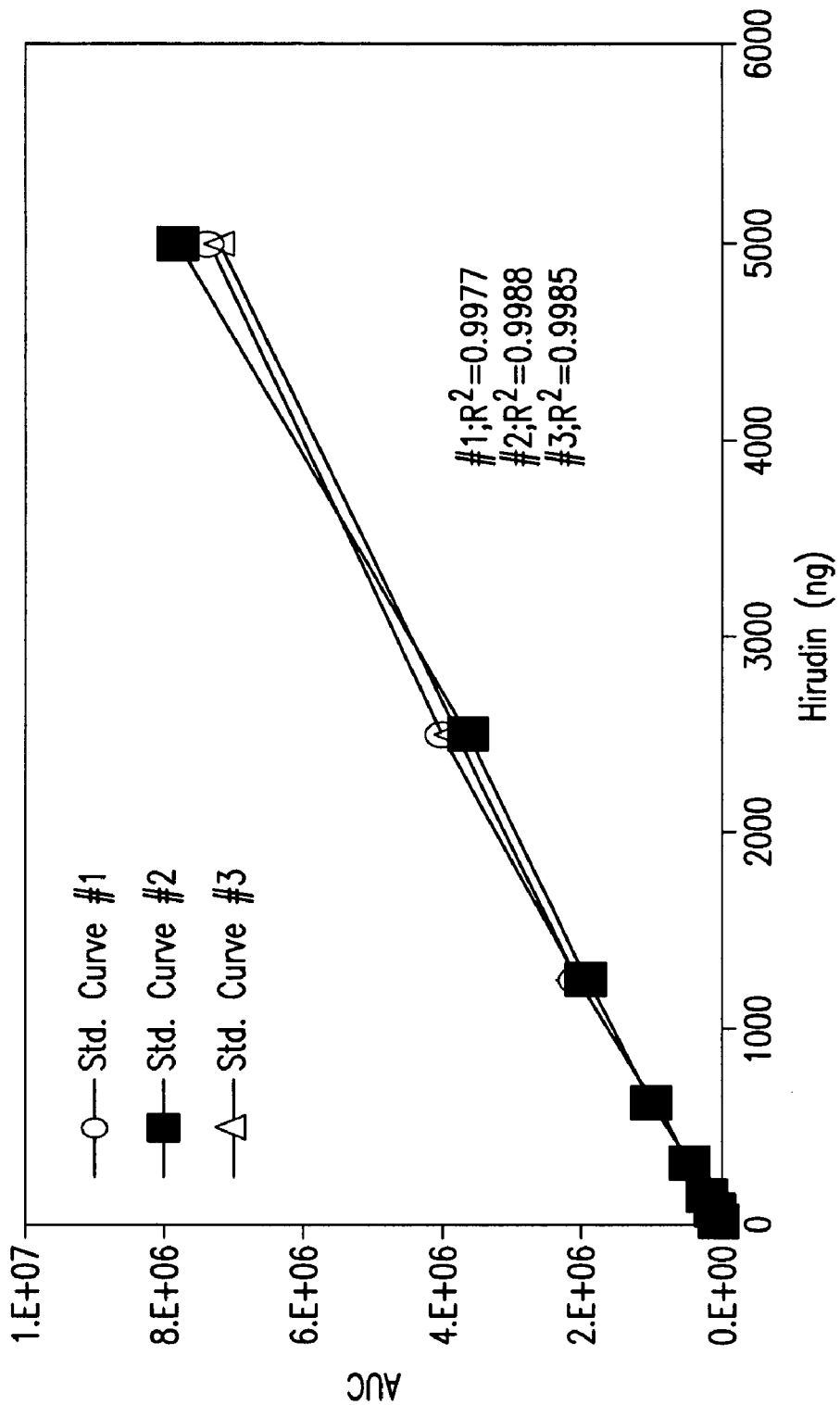
FIG. 9 shows an HPLC Standard Curve for Hirudin. Three standard curves for hirudin were generated using a C18 Nucleosil® 5 μm analytical column (4.6×250 mm). The mobile phase consisted of water:acetonitrile:trifluoroacetic acid (59.95:40:0.05 w/w/w). The flow rate was 0.6 mL/min. Each 50 μL sample of each standard curve was injected three times and the average AUC was plotted.

HPLC Assay for Hirudin: Three standard curves for hirudin were generated using a C18 Nucleosil® 5 μm analytical column (4.6×250 mm). The mobile phase consisted of water: acetonitrile:trifluoroacetic acid (59.95:40:0.05 w/w/w). The flow rate was 0.6 mL/min. Each 50 μL sample of each standard curve was injected three times and the average AUC was plotted as shown in FIG. 9.

The data suggested that wax-film composites containing either pre-loaded or post-loaded hirudin can be placed in the mouth of a warm-blooded animal to result in the absorption of hirudin into the systemic circulation in an amount suitable to elicit a pharmacological response (i.e., effect blood-clotting time).

Example 12

Figure 10:
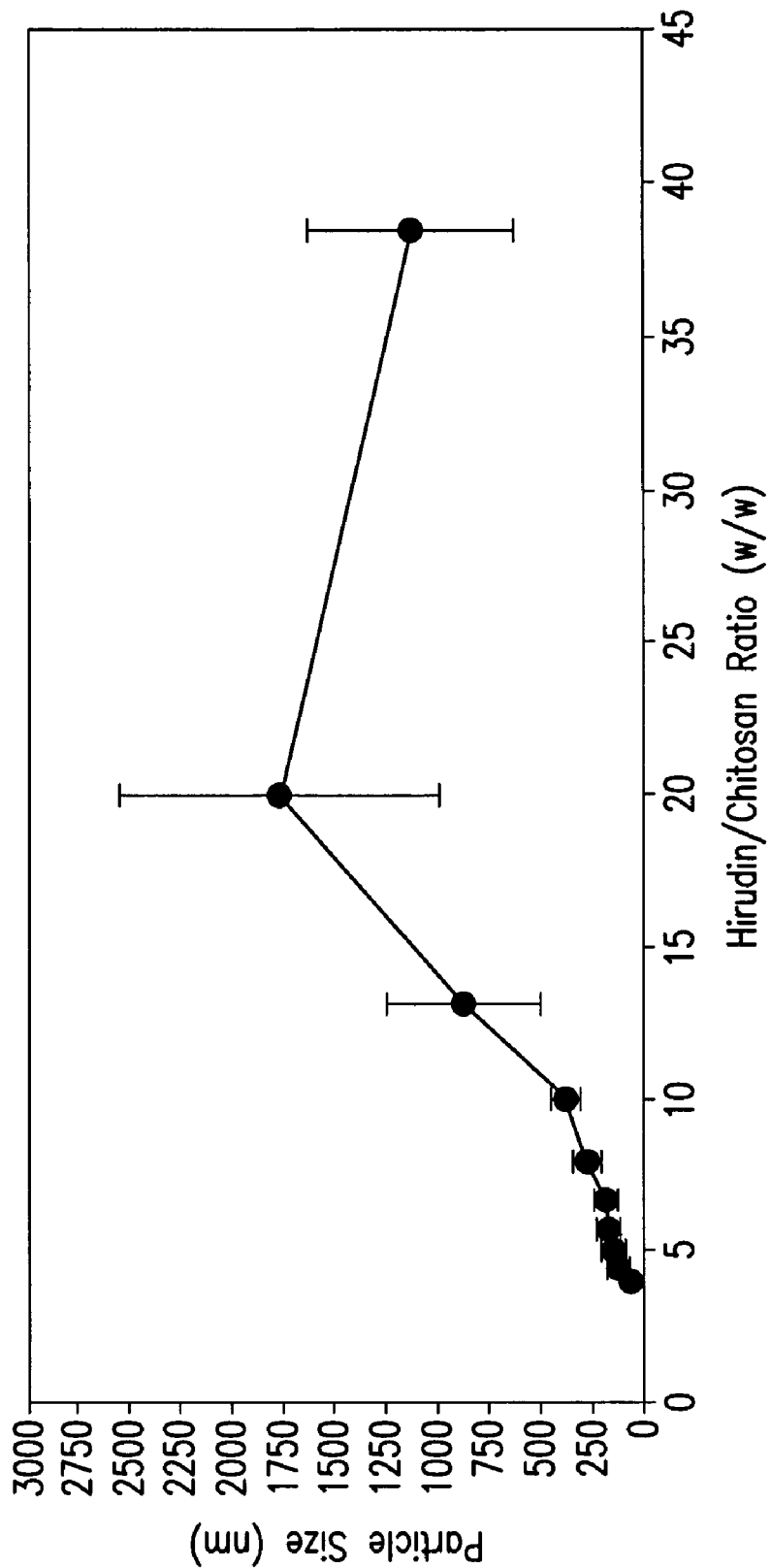
FIG. 10 shows the Particle Size of Hirudin/Chitosan Complexes in water made with hirudin at a Concentration of 0.5 mg/mL.
Figure 11:
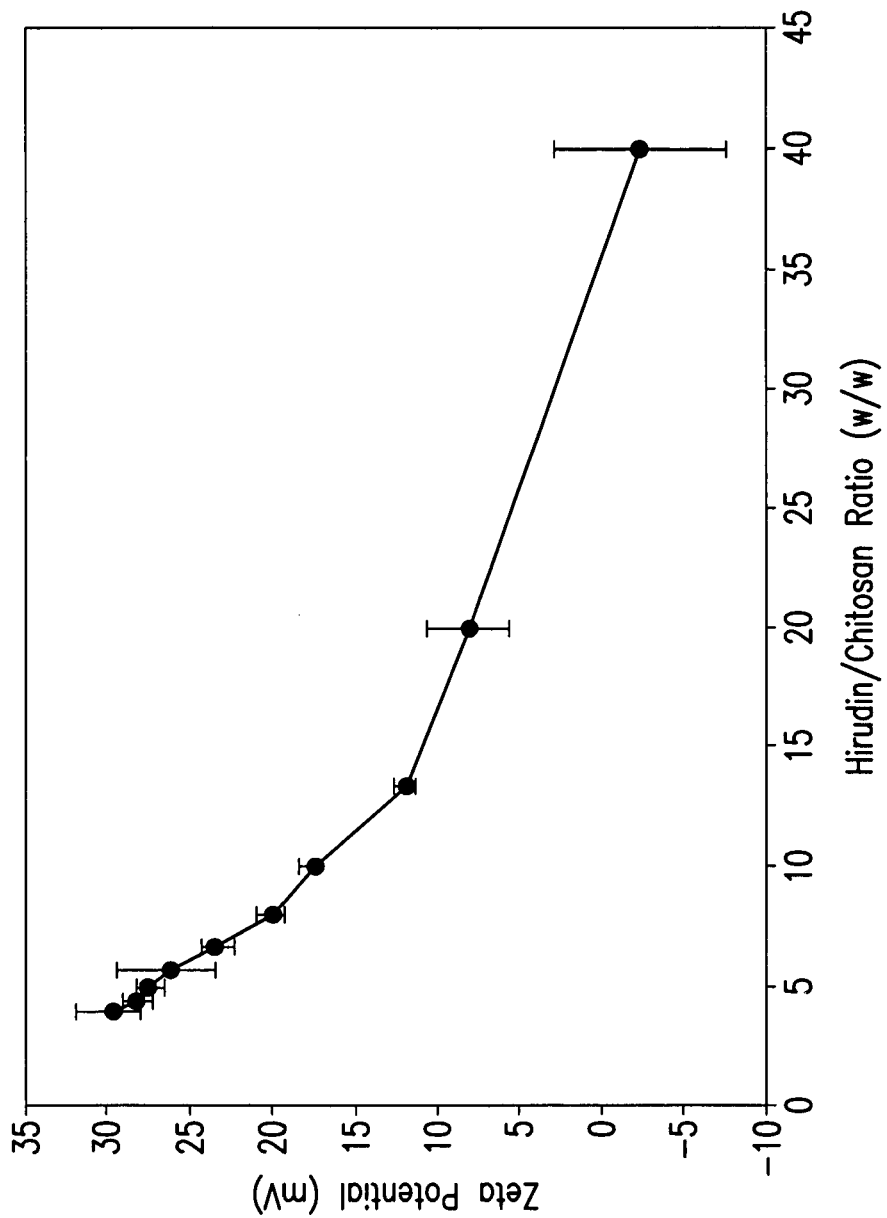
FIG. 11 shows the Zeta Potential of Hirudin/Chitosan Complexes in water made with Hirudin at a Concentration of 0.1 mg/mL. Zeta Potential values are reported as the mean and standard deviation of three measurements.
Figure 12:
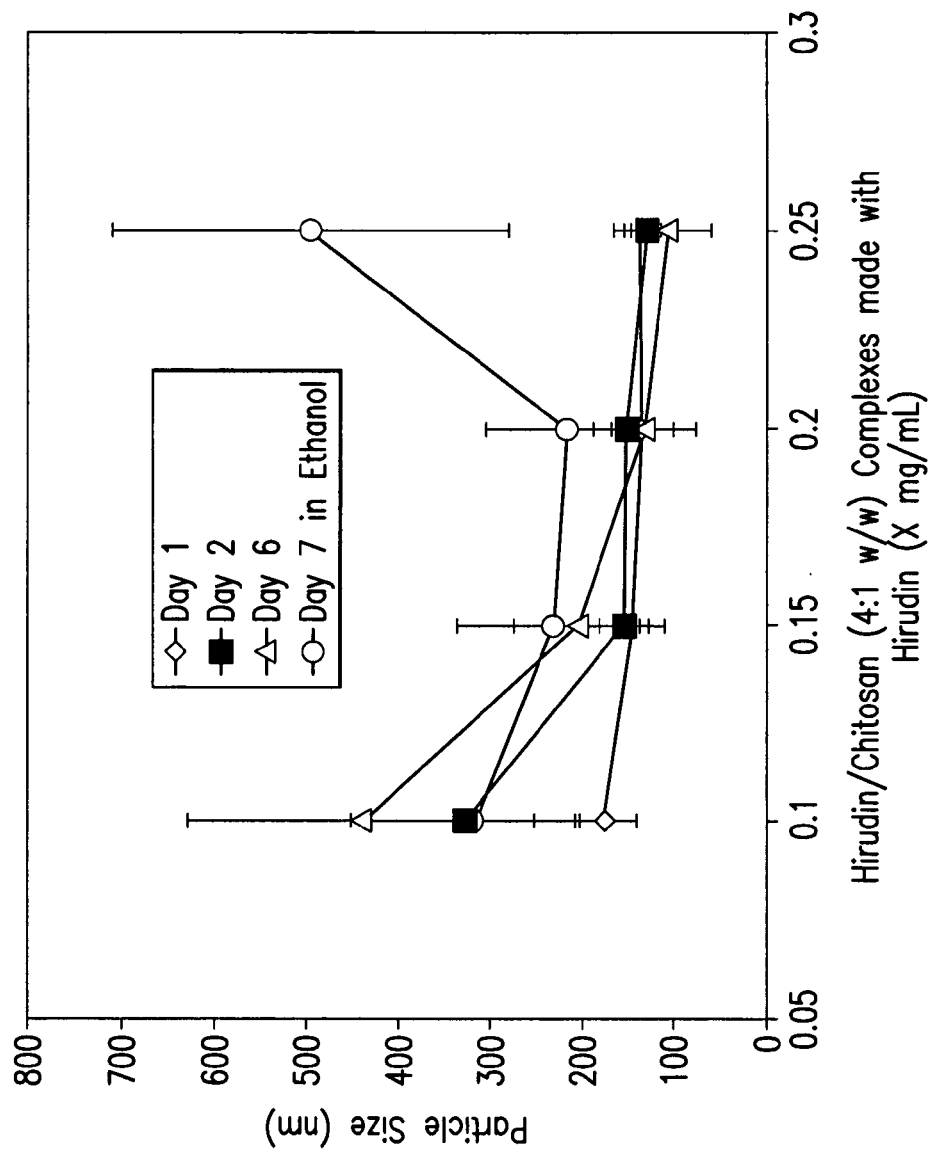
FIG. 12 shows the stability of Hirudin/Chitosan Complexes (4:1 w/w) made in water as function of Hirudin concentration and storage time. All samples were stored at 4° C. For the Day 7 sample analysis, exactly 100 μL of Hirudin/Chitosan complexes in water was diluted in 900 μL ethanol to determine the stability of the complexes in ethanol.

Hirudin/chitosan complexes were prepared by adding chitosan (from 13 μg to 125 μg) to hirudin (0.5 mg) in water so that the total volume was 1 mL. The particle size of the complexes was measured using a Coulter N4 Plus Sub-Micron Particle Sizer using 90° laser light scattering for 120 seconds. The results indicate that the complex size was effected by the weight ratio of hirudin and chitosan in solution with a hirudin/chitosan ratio of 4:1 w/w resulting in the smallest complex size of approximately 100 nm (FIG. 10). Hirudin/chitosan complexes were also prepared by adding chitosan (from 2.5 μg to 25 μg) to hirudin (0.1 mg) in water so that the total volume was 1 mL. The zeta potential of the complexes was measured using a Malvern Zetasizer 2000. The zeta potential results in millivolt (mV) indicated that as the weight ratio of hirudin to chitosan increased, the overall charge of the complex decreased (FIG. 11). This result was expected since hirudin is negatively-charged and chitosan is positively-charged. The particle size stability of selected complexes stored at 4° C. size was also determined. Four complexes having hirudin/chitosan weight ratios of 0.1, 0.15, 0.2, and 0.25 w/w were particle sized on Day 1, 2, 6, and 7 and the results are shown in FIG. 12. For the Day 7 sample analysis, exactly 100 μL of hirudin/chitosan complexes in water was diluted in 900 μL ethanol to determine the stability of the complexes in ethanol. The results showed that selected complexes were very stable when stored at 4° C. and when diluted into ethanol. These results suggest that selected hirudin/chitosan complexes could be incorporated into the wax-film composites as described in previous Examples and remain stable. Further, the results suggest that hirudin could be released from the wax-film composites and retain its ability to inhibit thrombin. Lastly, the results indicated that wax-film composites containing either pre-loaded or post-Loaded hirudin, complexed with chitosan, could be placed in the mouth of a warm-blooded animal to result in the absorption of hirudin into the systemic circulation in an amount suitable to elicit a pharmacological response (i.e., effect blood-clotting time).

All of the cited references are incorporated herein by reference in their entirety.

LITERATURE CITED

Aspden, T. J., Adler, J., Davis, S. S., Skaugrud, O., Illum, L. Chitosan as a nasal delivery system: evaluation of the effect of chitosan on mucociliary clearance rate in the frog palate model. *Int. J Pharm.* 122:69–78, 1995.

Bayley, D., Temple, C., Clay, V., Steward, A., Lowther, N. The transmucosal absorption of recombinant human interferon-alpha B/D hybrid in the rat and rabbit. *J. Pharm. Pharmacol.* 47:721–724, 1995.

Bechgaard, E., Gizurarson, S., Hjorkjaer, R. K. Solubilization of various benzodiazepines for intranasal administration, a pilot study. *Pharm. Dev. Tech.* 2:293–296, 1997.

Berthold, A., Cremer, K., Kreuter, J. Preparation and characterization of chitosan microspheres as drug carriers for prednisolone sodium phosphate as a model for anti-inflammatory drugs. *J. Cont. Rel.* 39:17–25, 1996.

Bhatt, L. C., Johnston, T. P. In vitro release and permeation of oxytocin from a mucoadhesive buccal patch. *Pharm. Dev. Technol.* 1:357–364, 1996.

Bhatt, L. C., Johnston, T. P. Transmucosal delivery of oxytocin to rabbits using a mucoadhesive buccal patch. *Pharm. Dev. Technol.* 2:265–274, 1997.

Binnie, W. H., Curro, F. A., Khandwala, A., Van Inwegan, R. G. Amlexanox oral paste: a novel treatment that accelerates the healing of aphthous ulcers. *Compend Contin Educ Dent.* 18:1116–1118, 1997.

Bodde, H. E., de Vries, M. E., Junginger, H. E. Mucoadhesive polymers for the buccal delivery of peptides, structure-adhesiveness relationships. *J. Cont. Rel.* 13:225–231, 1990.

Casetta, P., Negretti, F. Salivary immune responses after gingival immunization with tetravaccinal and bivaccinal formulations of inactivated micro-organisms. *Dev. Biol. Stand.* 92:317–321, 1998.

Chang, J. Y. Stability of hirudin, a thrombin-specific inhibitor. *J. Biol. Chem.* 266:10839–10843, 1991.

Duchene, D., Touchard, F., Peppas, N. A. Pharmaceutical and medical aspects of bioadhesive systems for drug administration. *Drug Devol. Ind. Pharm.* 14:283–318, 1988.

Eric, D., Caroline, E. Influence of storage conditions on the activity of recombinant hirudin. *Thromb Res.* 61:87–89, 1991.

Eriksson, B. I., Ekman, S., Lindbratt, S., Baur, M., Bach, D., Torholm, C., Kalebo, P., Close, P. Prevention of thromboembolism with use of recombinant hirudin. Results of a double-blind, multicenter trial comparing the efficacy of desirudin (Revasc) with that of unfractionated heparin in patients having a total hip replacement. *J Bone Joint Surg Am.* 79:326–33, 1997.

Esslinger, H. U., Haas, S., Maurer, R., Lassmann, A., Dubbers, K., Muller-Peltzer, H. Pharmacodynamic and safety results of PEG-hirudin in healthy volunteers. *Thromb. Haemost.* 77:911–919, 1997.

Etchart, N., Buckland, R., Liu, M. A., Wild, T. F., Kaiserlian, D. Class I-restricted CTL induction by mucosal immunization with naked DNA encoding measles virus hemagglutinin. *J. Gen. Virol.* 78:1577–1580, 1997.

Fenton, J. W. Thrombin interactions with hirudin. *Sem. Thromb. Hemost.* 15:265–268, 1989.

Fenton, J. W., Villanueva, G. B., Ofosu, F. A., Maraganore, J. M. Thrombin inhibition by hirudin: how hirudin inhibits thrombin. *Haemostasis,* 21:27–31, 1991.

Garcia-Closas, M., Herrero, R., Bratti, C., Hildesheim, A., Sherman, M. E., Morera, L. A., Schiffman, M. Epidemiologic determinants of vaginal pH. Am. J. Obstet. Gynecol. 180: 1060–1066.

Goto, S., Kawata, M., Suzuki, T., Kim, N. S., Ito, C. Preparation and evaluation of Eudragit gels. I: Eudragit organogels containing drugs as rectal sustained-release preparations. *J Pharm Sci.* 80:958–961, 1991.

Hardy, E., Jimenez, A. L., de Padue, K. S., Zaneveld, L. J. Women's preferences for vaginal antimicrobial contraceptives. III. Choice of a formulation, applicator, and packaging. Contraception. 58:245–249, 1998a.

Hardy, E., de Padu, K. S., Osis, M. J., Jimenez, A. L., Zaneveld, L. J. Women's preferences for vaginal antimicrobial contraceptives. IV. Attributes of a formulation that would protect from STD/AIDS. Contraception, 58:251–255, 1998b.

Harris, D., Robinson, J. R. Bioadhesive polymers in peptide and drug delivery. *Biomaterials,* 11:652–558, 1990.

Heath, R. J., Rubin, J. R., Holland, D. R., Zhang, E., Snow, M. E., Rock, C. O. Mechanism of triclosan inhibition of bacterial fatty acid synthesis. *J Biol Chem.* 1999 274:11110–11114, 1999.

Henriksen, I., Vagen, S. R., Sande, S. A., Smistad, G., Karlsen, J. Interactions between liposomes and chitosan II: effect of selected parameters on aggregation and leakage. *Int. J Pharm.* 146:193–204, 1997.

Hjortkjaer, R. K., Bechgaard, E., Gizurarson, S. Suzdak, C., McDonald, P., Greenough, R. J. Single- and repeated-dose local toxicity in the nasal cavity of rabbits after intranasal administration of different glycols for formulations containing benzodiazepines. *J. Pharm. Pharmacol.* 51:377–383, 1999.

Illum, L., Farraj, N. F., Davis, S. S. Chitosan as a novel nasal delivery system for peptide drugs. *Pharm. Res.* 11:1186–1189, 1994.

Imai, T., Shiraishi, S., Saito, H., Otagiri, M. Interaction of indomethacin with low molecular weight chitosan, and improvements of some pharmaceutical properties of indomethacin by low molecular weight chitosans. *Int. J. Pharm.* 67:11–20, 1991.

Jones, M. N., Francis, S. E., Hutchinson, F. J., Handley, P. S., Lyle, I. G. Targeting and delivery of bactericide to adsorbed oral bacteria by use of proteoliposomes. *Biochim Biophys Acta.* 1993 1147:251–261, 1993.

Kawata, M., Suzuki, T., Kim, N. S., Ito, T., Kurita, A., Miyagoe, Y., Goto, S. Preparation and evaluation of Eudragit gels. II: In vitro release of salicylic acid, sodium salicylate, and ketoprofen from Eudragit L and S organogels. *J Pharm Sci.* 80:1072–1074, 1991.

Khan, M. Z., Prebeg, Z., Kujakovic, N. A pH-dependent colon targeted oral drug delivery system using methacrylic acid copolymers. I. Manipulation of drug release using Eudragit L100–55 and Eudragit S100 combinations. *J Controlled Release.* 58:215–22, 1999.

Khandwala, A., Van Inwegen, R. G., Alfano, M. C. 5% amlexanox oral paste, a new treatment for recurrent minor aphthous ulcers: I. Clinical demonstration of acceleration of healing and resolution of pain. *Oral Surg Oral Med Oral Pathol Oral Radiol Endod.* 1997 83:222–230, 1997a.

Khandwala, A., Van Inwegen, R. G., Charney, M. R., Alfano, M. C. 5% amlexanox oral paste, a new treatment for recurrent minor aphthous ulcers: II. Pharmacokinetics and demonstration of clinical safety. *Oral Surg Oral Med Oral Pathol Oral Radiol Endod.* 83:231–238, 1997b.

Kim, N. S., Umejima, H., Ito, T., Uchida, T., Goto, S. Preparation and evaluation of Eudragit gels. V. Rectal gel preparations for sustained release and avoidance of first-pass metabolism of lidocaine. *Chem Pharm Bull.* 40:2800–2804, 1992a.

Kim, N. S., Ito, T., Kawata, M., Uchida, T., Goto, S. Preparation and evaluation of Eudragit gels. IV: Rectal gel preparations for sustained release and avoidance of first-pass metabolism of propentofylline. *J Pharm Sci.* 81:904–907, 1992b.

Kim, N. S., Kawata, M., Uchida, T., Goto, S. Preparation and evaluation of Eudragit gels. III: Rectal gel preparations for sustained release of pentoxifylline. *J Pharm Sci.* 81:537–40, 1992.

Lehr, C. M., Bouwstra, J. A., Schacht, E., Junginger, H. E. In vitro evaluation of mucoadhesive properties of chitosan and some other natural polymers. *Int. J Pharm.* 78:43–48, 1992.

Leopold, C. S., Eikeler. Eudragit E as a coating material for the pH-controlled drug release in the topical treatment of inflammatory bowel disease (IBD). *J. Drug Targeting.* 6:85–94, 1998.

Leung, S. H., Nagai, T., Machida, Y. Mucoadhesive dosage forms for peptide and protein drug delivery. In: *Peptide and Protein Drug Delivery.* V. H. L. Lee ed. Marcel Dekker, Inc. New York, pp. 741–767, 1991.

Liu, M. A., Hilleman, M. R., and Kurth, R., eds. (1995). *DNA Vaccines: A New Era in Vaccinology.* Vol. 772. Ann. N.Y. Acad. Sci. New York, N.Y.

Loftsson, T., Leeves, N., Bjornsdottir, B., Duffy, L., Masson, M. Effect of cyclodextrins and polymers on triclosan availability and substantivity in toothpastes in vivo. *J Pharm Sci.* 88:1254–1258, 1999.

MacLaughlin, F. C, Mumper, R. J., Wang, J., Tagliaferri, J. M., and Rolland, A. P. Chitosan and depolymerized chitosan oligomers as condensing carriers for in-vivo plasmid delivery. *J. Controlled Rel.* 56:259–272, 1998.

Mandel, I. D. Antimicrobial mouthrinses: overview and update. *J Am Dent Assoc.* 125:2S–10S, 1994.

March, C., Nakamura, R. Evaluation of the duration of effect of a bioadhesive vaginal moisturizing gel on vaginal pH. 7th International Congress on the Menopause, Replens Symposium. Stockholm, Sweden, Jun. 20–22, 1993.

Markwardt, F. Development of hirudin as an antithrombotic agent. *Sem. Thromb. Hemost.* 15:269–282, 1989.

Markwardt, F. Hirudin and derivatives as anticoagulant agents. *Thromb. Haemost.* 66:141–152, 1991a.

Markwardt, F. Past, present and future of hirudin. *Haemostatis,* 21:11–26, 1991b.

Martin's Physical Pharmacy: Physical Chemical Principles in the Pharmaceutical Sciences. A. Martin, J. Swarbrick, A. Cammarata, eds. Third Edition. Lea & Febiger, Philadelphia. 1983.

McGhee, J. R., Kiyono, H. (1992a). Mucosal immunity to vaccines: Current concepts for vaccine development and immune response analysis. In: J. E. Ciardi (ed.) *Genetically engineered vaccines.* Plenum Press, New York, N.Y. pp. 3–12.

Meshali, M. M., Gabr, K. E. Effect of interpolymer complex formation of chitosan with pectin or acacia on the release behavior of chlorpromazine HCl. *Int. J. Pharm.* 89:177–181, 1993.

Park, H., Robinson, J. R. Physico-chemical properties of water insoluble polymers important to mucin/epithelial adhesion. J. Cont. Rel. 2:47–57, 1985.

Peniston, Q. P., Johnson, E. L. Process for depolymerization of chitosan. U.S. Pat. No. 3, 922,260, Nov. 25, 1975.

Remington's Pharmaceutical Sciences. 18th Edition. A. R. Gennaro, ed. Mack Publishing Company, Easton, Pa., 1990.

Riehl-Bellon, N., Carvallo, D., Acker, M., Van Dorsselaer, A., Marquet, M., Loison, G., Lemoine, Y., Brown, S. W., Courtney, M., Roitsch, C. Purification and biochemical characterization of recombinant hirudin produced by *Saccharomyces cerevisiae*. *Biochemistry*, 28:2941–2949, 1989.

Robinson, H. L., Torres, C. A. T. DNA Vaccines. *Sem. Immun.* 9:271–283, 1997.

Rathbone, M., Ponchel, G., Ghazali, F. in *Oral Mucosal Drug Delivery*, M. J. Rathbone Ed., Marcel Dekker Inc. New York, 1996.

Saijo, T., Kuriki, H., Ashida, Y., Makino, H., Maki, Y. Inhibition by amoxanox (AA-673) of the immunologically, leukotriene D4- or platelet-activating factor-stimulated bronchoconstriction in guinea pigs and rats. *Int Arch Allergy Appl Immunol.* 77:315–321, 1985.

Saijo, T., Makino, H., Tamura, S., Kuriki, H., Ashida, Y., Terao, S., Maki, Y. The antiallergic agent amoxanox suppresses SRS-A generation by inhibiting lipoxygenase. *Int Arch Allergy Appl Immunol.* 79:231–237, 1986.

Sayani, A. P., Chun, I. K., Chien, Y. W. Transmucosal delivery of leucine enkephalin: stabilization in rabbit enzyme extracts and enhancement of permeation through mucosae. *J. Pharm. Sci.* 82:1179–1185, 1993.

Schipper, N. G. M., Varum, K. M., Artursson, P. Chitosans as absorption enhancers for poorly absorbable drugs. I: influence of molecular weight and degree of acetylation on drug transport across human intestinal epithelial (Caco-2) cells. *Pharm. Res.* 13:1686–1692, 1996.

Schwagmeier, R., Alincic, S., Striebel, H. W. Midazolam pharmacokinetics following intravenous and buccal administration. *Br. J. Clin. Pharmacol.* 46:203–206, 1998.

Scott, R. C., Besag, F. M. C., Neville, B. G. R. Buccal midazolam and rectal diazepam for treatment of prolonged seizures in childhood and adolescence: a randomized trial. *The Lancet.* 353:623–626, 1999.

Shiraishi, S., Imai, T., Otagiri, M. Controlled release of indomethacin by chitosan-polyelectrolyte complex: optimization and in vivo/in vitro evaluation. *J. Cont. Rel.* 25:217–225, 1993.

Spannagl, M., Bichler, H., Lill, H., Schramm, W. A fast photometric assay for the determination of hirudin. *Haemostasis.* 21:36–40,1991.

Stevens-Simon, C., Jamison, J., McGregor, J. A., Douglas, J. M. Racial variation in vaginal pH among healthy sexually active adolescents. Sex. Transm. Dis. 21:168–172, 1994.

Takayama, K., Hirata, M., Machida, Y., Masada, T., Sannan, T., Nagai, T. Effect of interpolymer complex formation on bioadhesive property and drug release phenomenon of compressed tablet consisting of chitosan and sodium hyaluronate. *Chem. Pharm. Bull.,* 38:1993–1997, 1990.

Takeuchi, H., Yamamoto, H., Niwa, T., Hino, T., Kawashima, Y. Enteral absorption of insulin in rats from mucoadhesive chitosan-coated liposomes. *Pharm. Res.* 13:896–901, 1996.

Tang, D. C., DeVit, M., Johnston, S. A. Genetic immunization is a simple method for eliciting an immune response. *Nature* 356:152–154, 1992.

Taubes, G. Salvation in a snippet of DNA. *Science* 278: 1711–1714, 1997.

Ulmer, J. B., Donnelly, J. J., Liu, M. A. Toward the development of DNA vaccines. *Curr. Opin. Immun.* 8:531–536, 1996a.

Umejima, H., Kim, N. S., Ito, T., Uchida, T., Goto, S. Preparation and evaluation of Eudragit gels. VI: In vivo evaluation of Eudragit rectal hydrogel and xerogel containing salicylamide. *J Pharm Sci.* 82:195–9, 1993.

Urisu, A., Iimi, K., Kondo, Y., Horiba, F., Masuda, S., Tsuruta, M., Yazaki, T., Torii, S. Inhibitory action amlexanox on interleukin-3-induced enhancement of histamine releasability of human leukocytes. *Arerugi.* 39(10): 1448–1454, 1990.

Wong, C. F., Yuen, K. H., Peh, K. K. Formulation and evaluation of controlled release Eudragit buccal patches. *Int. J. Pharmaceutics.* 178:11–22, 1999.

Yankauckas, M. A., Morrow, J. E., Parker, S. E., Abai, A., Rhodes, G. H., Dwarki, V. J., and Gromkowski, S. H. Long-term anti-nucleoprotein cellular and humoral immunity is induced by intramuscular injection of plasmid DNA containing NP gene. *DNA Cell. Biol.* 12:771–776, 1993.

Zuckerbraun, H. L., Babich, H., May, R., Sinensky, M. C. Triclosan: cytotoxicity, mode of action, and induction of apoptosis in human gingival cells in vitro. *Eur J Oral Sci.* 1998 106:628–636, 1998.

What is claimed is:

1. A pharmaceutical gel comprising:
    a solvent vehicle comprising 25 to 100 parts by weight water or buffered water and 0 to 75 parts by weight of ethanol, propylene glycol, glycerin, polyethylene glycol, or combinations thereof, where the solvent vehicle is 100 parts by weight total;
    at least one water-insoluble swellable mucoadhesive polymer, wherein the water-insoluble swellable mucoadhesive polymer is crossed-linked polyacrylic acid;
    at least one pH-sensitive anionic copolymer of methacrylic acid and methacrylic acid esters, which forms a film when applied to skin or a mucosal surface, and
    at least one molecule of interest.

2. The composition of claim 1, wherein the water-insoluble swellable mucoadhesive polymer is polyacrylic acid cross-linked with polyalkenyl ether or divinyl glycol.

3. The composition of claim 1, wherein the water-insoluble swellable mucoadhesive polymer is NOVEON or CARBOMER.

4. The composition of claim 1, wherein the water-insoluble swellable mucoadhesive polymer is present at a concentration of from 0.1% to 20% by weight.

5. The composition of claim 1, wherein the pH-sensitive polymer is present at a concentration of from 0.05% to 10% by weight.

6. The composition of claim 1, wherein the pH-sensitive polymer is a EUDRAGIT polymer.

7. The composition of claim 1, wherein the molecule of interest comprises an active pharmaceutical.

8. The composition of claim 1, wherein the molecule of interest is amlexanox.

9. The composition of claim 1, wherein the molecule of interest is triclosan.

10. The composition of claim 1, wherein the molecule of interest is hirudin.

11. The composition of claim 1, wherein the molecule of interest is plasmid DNA.

12. The composition of claim 1, wherein the molecule of interest is lidocaine, benzocaine, or dyclonine.

13. The composition of claim 1, wherein the molecule of interest is at least one benzodiazepine drug.

14. The gel of claim 1, wherein the molecule of interest is a peptide or protein.

15. The gel of claim 7, wherein the active pharmaceutical comprises an antimicrobial, antiviral, antiinflammatory, antiseptic, antihistamine, a local anesthetic, a disinfectant, a keratolytic, an analgesic, an anti-migraine, an anti-fungal, a sweetener, a flavoring agent, a diagnostic agent, or combination thereof.

* * * * *

UNITED STATES PATENT AND TRADEMARK OFFICE
CERTIFICATE OF CORRECTION

| | | |
|---|---|---|
| PATENT NO. | : 7,803,392 B2 | Page 1 of 1 |
| APPLICATION NO. | : 09/748133 | |
| DATED | : September 28, 2010 | |
| INVENTOR(S) | : Mumper et al. | |

It is certified that error appears in the above-identified patent and that said Letters Patent is hereby corrected as shown below:

Claim 2, column 28, line 46, please replace "composition" with -- gel --.

Claim 3, column 28, line 49, please replace "composition" with -- gel --.

Claim 4, column 28, line 52, please replace "composition" with -- gel --.

Claim 5, column 28, line 55, please replace "composition" with -- gel --.

Claim 6, column 28, line 58, please replace "composition" with -- gel --.

Claim 7, column 28, line 60, please replace "composition" with -- gel --.

Claim 8, column 28, line 62, please replace "composition" with -- gel --.

Claim 9, column 28, line 64, please replace "composition" with -- gel --.

Claim 10, column 28, line 66, please replace "composition" with -- gel --.

Claim 11, column 29, line 1, please replace "composition" with -- gel --.

Claim 12, column 29, line 3, please replace "composition" with -- gel --.

Claim 13, column 29, line 5, please replace "composition" with -- gel --.

Signed and Sealed this
Twenty-first Day of June, 2011

David J. Kappos
*Director of the United States Patent and Trademark Office*